(12) United States Patent
Oreper et al.

(10) Patent No.: US 7,899,156 B2
(45) Date of Patent: Mar. 1, 2011

(54) IRRADIATION SYSTEM INCLUDING AN ELECTRON-BEAM SCANNER

(75) Inventors: Boris Oreper, Newton, MA (US);
Douglas P. Boyd, Las Vegas, NV (US);
Nikolay Rolshud, Winchester, MA (US)

(73) Assignee: L-3 Communications Security and Detection Systems, Inc., Woburn, MA (US)

( * ) Notice: Subject to any disclaimer, the term of this patent is extended or adjusted under 35 U.S.C. 154(b) by 0 days.

(21) Appl. No.: 12/503,560

(22) Filed: Jul. 15, 2009

(65) Prior Publication Data

US 2010/0014638 A1    Jan. 21, 2010

Related U.S. Application Data

(60) Provisional application No. 61/094,549, filed on Sep. 5, 2008, provisional application No. 61/081,360, filed on Jul. 16, 2008.

(51) Int. Cl.
    *A61N 5/10* (2006.01)
(52) U.S. Cl. ............................................ 378/65; 378/205
(58) Field of Classification Search .................... 378/64, 378/65, 205
    See application file for complete search history.

(56) References Cited

U.S. PATENT DOCUMENTS

| | | |
|---|---|---|
| 3,983,398 A | 9/1976 | Boyd |
| 4,075,491 A | 2/1978 | Boyd |
| 4,138,721 A | 2/1979 | Boyd |
| 4,144,492 A | 3/1979 | Zschimmer |
| 4,274,005 A | 6/1981 | Yamamura et al. |
| 4,352,021 A | 9/1982 | Boyd et al. |
| 4,521,901 A | 6/1985 | Rand |
| 4,631,741 A | 12/1986 | Rand et al. |
| 4,736,396 A | 4/1988 | Boyd et al. |
| 4,977,585 A | 12/1990 | Boyd |
| 4,993,055 A | 2/1991 | Rand et al. |

(Continued)

FOREIGN PATENT DOCUMENTS

WO    WO 02/43565 A1    6/2002

OTHER PUBLICATIONS

International Search Report and Written Opinion for corresponding International Application No. PCT/US2009/050743, mailed Sep. 10, 2009, 11 pages.

(Continued)

*Primary Examiner* — Hoon Song
(74) *Attorney, Agent, or Firm* — Fish & Richardson P.C.

(57) ABSTRACT

A property of a treatment beam is controlled during a scanning period. A portion of a region is exposed to an imaging x-ray beam during a scanning period, the imaging x-ray beam being generated by an electron-beam scanner. X-ray radiation from the region is detected, the x-ray radiation representing an attenuation of the imaging x-ray beam caused by the portion of the region. A first image of the portion of the region is generated based on the detected x-ray radiation. A characteristic of the portion of the region is determined from the generated first image. An input derived from the characteristic is generated, the input configured to cause a source of a treatment beam to modify a property of the treatment beam. The source of the treatment beam modifies a property of the treatment beam during the scanning period by providing the input to the source of the treatment beam.

14 Claims, 19 Drawing Sheets

U.S. PATENT DOCUMENTS

| | | | |
|---|---|---|---|
| 4,998,268 | A | 3/1991 | Winter |
| 5,014,293 | A | 5/1991 | Boyd et al. |
| 5,105,456 | A | 4/1992 | Rand et al. |
| 5,144,492 | A | 9/1992 | Iijima et al. |
| 5,224,137 | A | 6/1993 | Plomgren et al. |
| 5,491,734 | A | 2/1996 | Boyd et al. |
| 5,721,889 | A | 2/1998 | Miller et al. |
| 5,999,587 | A | 12/1999 | Ning et al. |
| 6,144,492 | A | 11/2000 | Iwamura et al. |
| 6,385,288 | B1 * | 5/2002 | Kanematsu ............. 378/65 |
| 6,445,766 | B1 * | 9/2002 | Whitham ............. 378/65 |
| 6,628,745 | B1 | 9/2003 | Annis et al. |
| 6,735,271 | B1 | 5/2004 | Rand et al. |
| 6,839,404 | B2 | 1/2005 | Clark et al. |
| 7,023,950 | B1 | 4/2006 | Annis |
| 7,046,762 | B2 | 5/2006 | Lee |
| 7,233,644 | B1 | 6/2007 | Bendahan et al. |
| 7,428,297 | B2 | 9/2008 | Eilbert |
| 2003/0086529 | A1 | 5/2003 | Clark et al. |
| 2004/0165696 | A1 | 8/2004 | Lee |
| 2005/0058242 | A1 | 3/2005 | Peschmann |
| 2008/0063147 | A1 | 3/2008 | Juschka et al. |
| 2009/0180589 | A1 * | 7/2009 | Wang et al. ............. 378/65 |

OTHER PUBLICATIONS

"Mitsubishi Electron Beam Irradiation System," Mitsubishi Heavy Industries, Ltd., 1994-2008, reprinted on Aug. 27, 2008 from http://www.mhi.co.jp/en/products/category/mitsubishi_electron_beam_irradiation_system.html.

* cited by examiner

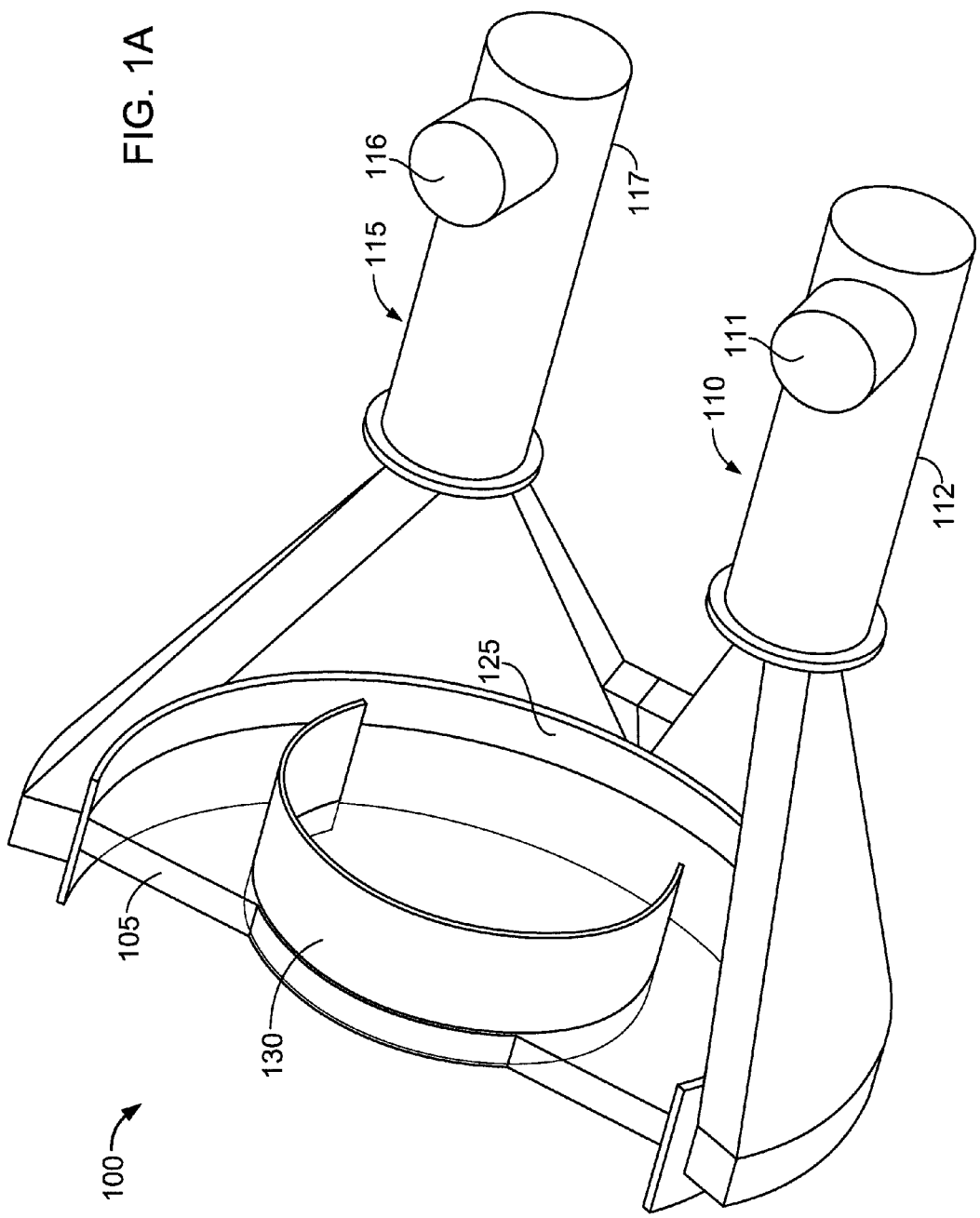

IRRADIATION SYSTEM INCLUDING AN ELECTRON-BEAM SCANNER

CROSS-REFERENCE TO RELATED APPLICATIONS

This application claims the benefit of U.S. Provisional Application Ser. No. 61/094,549 titled IRRADIATION SYSTEM INCLUDING AN ELECTRON-BEAM SCANNER and filed on Sep. 5, 2008, and U.S. Provisional Application Ser. No. 61/081,360, titled IRRADIATION WITH E-BEAM SCANNER and filed on Jul. 16, 2008, both of which are incorporated by reference in their entirety.

TECHNICAL FIELD

This disclosure relates to an irradiation system that includes an electron-beam scanner.

BACKGROUND

Computer tomography (CT) systems can be used to image a patient, including, for example, a patient's tumor. An irradiation system can deliver high-energy radiation, such as x-ray radiation, to the tumor to destroy the tumor.

SUMMARY

In one general aspect, a system includes an electron-beam scanner, a source of irradiation energy, and a processor. The electron-beam scanner includes an electron emitter configured to produce an electron beam, an electron accelerator configured to accelerate the electron beam toward a target that produces an x-ray beam in response to being struck by the electron beam, a steering device configured to scan the electron beam along the target such that the produced x-ray beam is positioned relative to a portion of a region to be imaged, and a detector configured to sense x-ray radiation from the region and produce a representation of the sensed radiation. The source of irradiation energy is configured to produce a treatment beam. The electron beam scanner and the source of irradiation energy are positioned to allow the portion of the region to be exposed to the treatment beam and the produced x-ray beam concurrently. The system also includes a processor operable to receive the representation of the sensed x-ray radiation, determine a characteristic of the imaged portion of the region based on the representation of the sensed x-ray radiation, and modify a property of the treatment beam based on the characteristic.

Implementations may include one or more of the following features. The electron beam scanner may be positioned at an angle relative to a direction of propagation of the treatment beam. The system also may include a gantry, and the electron beam scanner and the source of irradiation energy may both be located within the gantry. The electron-beam scanner may be movable with respect to the gantry and the processor may be further operable to determine a position of the electron-beam scanner relative to the gantry and a position of the produced x-ray beam relative to the gantry.

In some implementations, the characteristic of the portion of the region may include one or more of a position of the portion, a size of the portion, and a shape of the portion. The processor may be further operable to generate an image of the region based on the representation of the sensed radiation. The portion may include a biological structure within a human patient. The region may include a pancreas, and the portion of the region may include a portion of the pancreas.

To control the treatment beam based on the characteristic, the processor may be further operable to provide an input to the source of irradiation energy, the input being derived from the characteristic of the portion of the region and the input being sufficient to cause the source of irradiation energy to modify a property of the treatment beam. The processor may provide the input to the source of irradiation energy while the produced x-ray beam illuminates the portion of the region. The processor may provide the input to the source of irradiation energy while the portion of the region is imaged by the x-ray beam. The processor may provide input to the source of irradiation energy during a treatment session. The property of the treatment beam may include one or more of a beam profile of the treatment beam and an intensity of the treatment beam. The characteristic of the object may include a size and shape of the object, and the input to the source of irradiation energy may be sufficient to cause the source of irradiation energy to modify a beam profile of the treatment beam such that the profile approximately matches a size and shape of the object.

In another general aspect, during a scanning period in which a portion of a region is imaged by an electron-beam scanner, first data produced by the electron-beam scanner is received. The first data includes a first indication of a characteristic of the portion. During the scanning period, a characteristic of the portion from the first data is determined. During the scanning period, a first input derived from the characteristic is provided to a source of a treatment beam, the first input being sufficient to cause the source of the treatment beam to modify a property of the treatment beam. During the scanning period, second data produced by the electron-beam scanner is received. The second data is received after the first data and the second data includes a second indication of the characteristic of the portion. During the scanning period, the characteristic of the portion from the second data is determined. During the scanning period, a second input derived from the characteristic determined from the second data is provided to the source of an irradiation beam, the second input being sufficient to cause the source of the treatment beam to modify the property of the treatment beam to account for the characteristic determined from the second data.

Implementations may include one or more of the following features. The property of the treatment beam may include a beam profile of the treatment beam. The characteristic of the portion may include a shape of the portion, and the shape of the portion may vary during the scanning period. The portion may move during the scanning period. The region may include a human patient and the portion of the region may include a biological structure within the human patient. The property of the treatment beam may be a beam profile of the treatment beam and the first input and the second input are inputs sufficient to cause a leaf of a multi-leaf collimator coupled to the source of the treatment beam to move such that the beam profile is modified. The characteristic of the portion of the region may be a position, and the first input and the second input are inputs sufficient to cause the source of the treatment beam to direct the treatment beam toward the position of the portion. The portion of the region may include a biological structure of a patient, and the scanning period may be a continuous treatment session during which the patient remains in the region and the treatment beam irradiates the biological structure.

In some implementations, the second input may be provided to the source of the irradiation beam no more than one hundred milliseconds after the first input is provided to the source of the irradiation beam.

In another general aspect, a treatment beam is controlled during a scanning period. A portion of a region is exposed to an imaging x-ray beam during a scanning period, the imaging x-ray beam being generated by an electron-beam scanner. X-ray radiation from the region is detected, the x-ray radiation representing an attenuation of the imaging x-ray beam caused by the portion of the region. A first image of the portion of the region is generated based on the detected x-ray radiation. A characteristic of the portion of the region is determined from the generated first image. An input derived from the characteristic is generated, the input configured to cause a source of a treatment beam to modify a property of the treatment beam. The source of the treatment beam modifies a property of the treatment beam during the scanning period by providing the input to the source of the treatment beam.

Implementations may include one or more of the following features. The characteristic of the portion may include the position of the portion, and causing the source of the treatment beam to modify a property of the treatment beam may include modifying a direction of propagation of the treatment beam such that the treatment beam irradiates the portion.

In another general aspect, an apparatus to control a treatment beam based on data from an electron-beam scanner is assembled. A source of an irradiation energy configured to produce a treatment beam is positioned in a housing, and an electron-beam scanner configured to produce an x-ray imaging beam is positioned in the housing relative to the source of irradiation energy. The positioning of the electron-beam scanner allows an object in a region within the housing to be exposed to the treatment beam and the x-ray imaging beam concurrently.

Implementations of the techniques discussed above may include a method or process, a system or apparatus, or computer software on a computer-readable medium.

DESCRIPTION OF THE DRAWINGS

FIGS. 1A and 1B illustrate perspective views of a circular configuration electron-beam scanner.

Like reference numbers refer to like elements.

DETAILED DESCRIPTION

An electron-beam scanner capable of rapidly imaging a region of a patient (such as a tumor) can be combined with an irradiation system that delivers high-energy radiation (which may be referred to as a treatment beam) to the tumor imaged by the electron-beam scanner. The electron-beam scanner (e-beam scanner) scans a region at a rate of ten scans per second or higher and, thus, is able to generate clear images of the region even if the region (or a portion of the region) moves. The images generated by the electron-beam scanner are used to control and shape the treatment beam such that the treatment beam matches the imaged region or portion thereof, for example a tumor within or on the imaged region of the patient. In this manner, the amount of radiation delivered to the tumor may be increased relative to the amount of radiation delivered to the surrounding tissue. For convenience, area within or on a patient (such as, for example, a tumor, an organ, a portion of an organ, or another type of biological structure) that is to receive treatment may be referred to as an object.

Figure 1B:
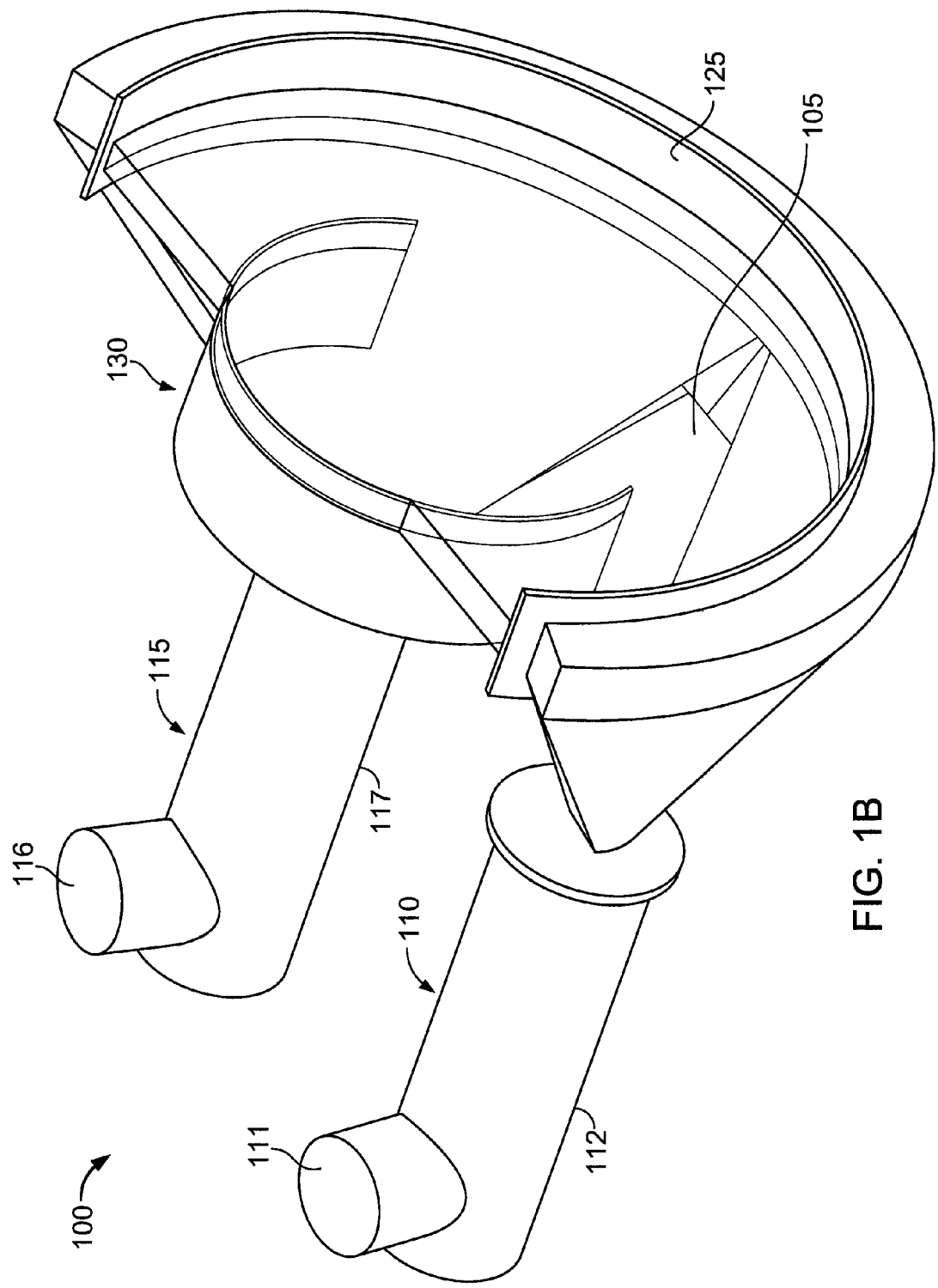
Figure 2:
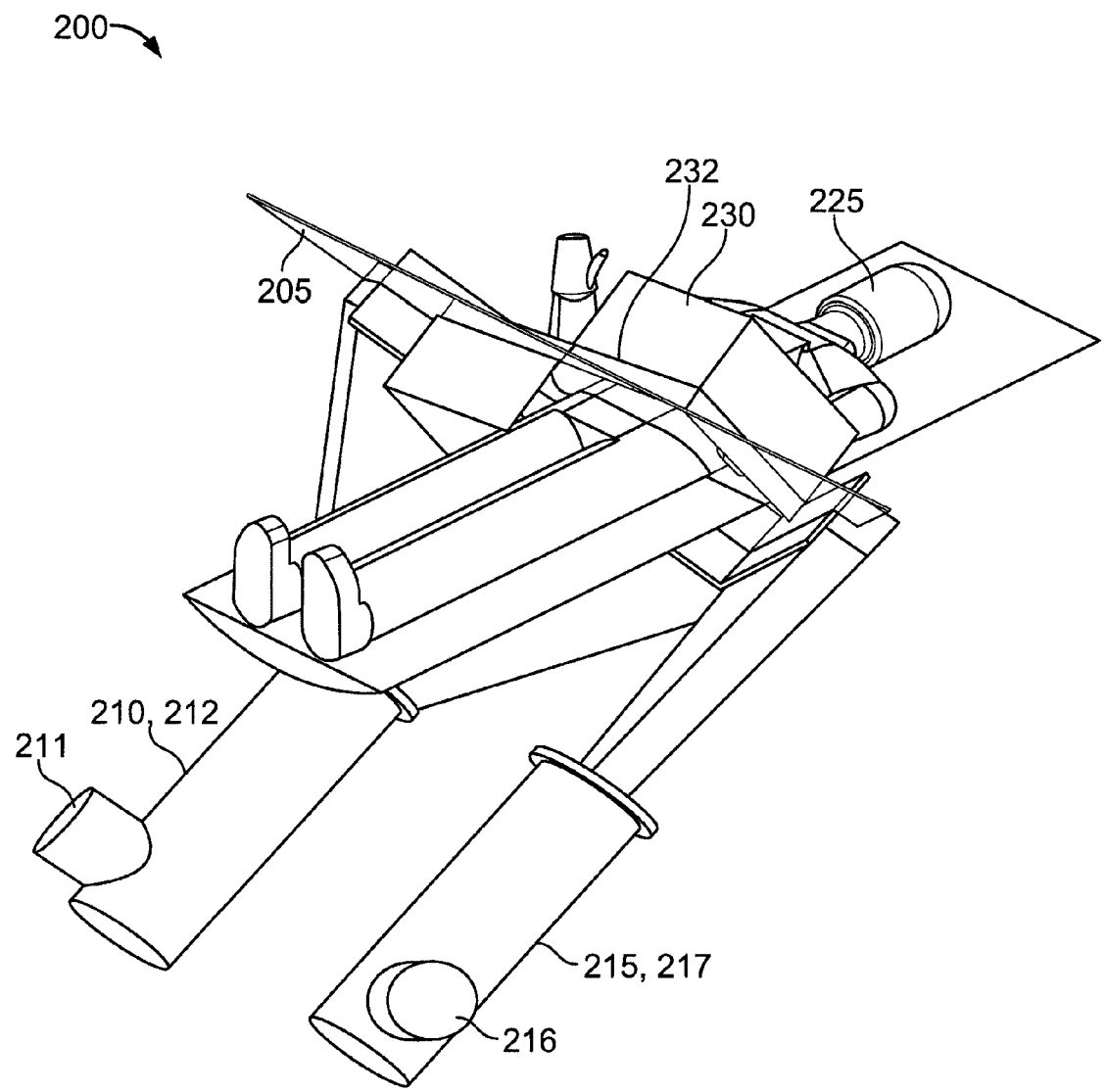
FIG. 2 illustrates an example of a linear configuration electron-beam scanner.

Referring to FIGS. 1A and 1B, an example electron-beam scanner 100 scans a region 105 with an electron beam generated from a first electron emitter 110 and a second electron emitter 115. The first and second electron emitters may be electron guns that emit a beam of electrons. In some implementations, the first and second electron emitters may be thermionic emitters, electron emitters made from carbon nanotubes, or photo emitters. The first and second electron emitters may both be the same type of emitter, or the first and second electron emitters may each be a different type of emitter. FIG. 1A shows a rear perspective view of the electron-beam scanner 100 and FIG. 1B shows a front perspective view of the electron-scanner 100. The electron-beam scanner 100 is a circular configuration of an electron-beam scanner. Other implementations may include different configurations, such as a linear configuration of the electron beam scanner. For example, FIG. 2 shows a linear configuration of an electron-beam scanner.

The electron beam from the electron guns 110 and 115 creates a scan beam (not shown) within the region 105. The scan beam scans the region 105 at a rate of ten scans per second or higher (for example, about fifty scans per second) to image objects within the region 105 (such as a portion of a human patient, a biological structure, or a tumor within the patient). The object may be considered to be a portion of the region 105. Because the region 105 is scanned at a rate of at least ten scans per second, tumors within the patient that move as a result of normal bodily functions (even when a person is lying still or attempting not to move), such as a tumor in or around the patient's lungs that moves continuously as the patient breathes, may be imaged as the tumors move. Scanning the region 105 at a rate of at least ten scans per second allows clear, non-blurred images of the moving tumors to be generated. Thus, the images generated by scanning the region 105 may be used to determine a profile or shape of a tumor within the patient as the tumor moves due to normal bodily functions.

The electron-beam scanner 100 is combined with an irradiation system (not shown) that delivers a high-energy radiation treatment beam (such as gamma radiation or x-ray radiation) to the tumors in order to destroy the tumor. By combining the electron-beam scanner 100 with the irradiation system, the images generated from the electron-beam scanner 100 may be used to control a property of the treatment beam, such as the direction and/or beam shape of the treatment beam, provided by the irradiation system. In particular, the determined profile of the tumor is used to digitally control a beam profile and position of the treatment beam from the irradiation system. Digitally controlling the beam profile and position of the treatment beam allows the treatment beam to be matched to the tumor such that the tumor receives as much radiation as possible (thus helping to ensure that the tumor is destroyed) while also preventing or minimizing the exposure of nearby tissues and structures to the treatment beam (thus helping to prevent damage to the nearby tissue and structures). Additionally, because the electron-beam scanning system 100 scans the region 105 at a rate of at least ten scans per second, the treatment beam can be quickly adjusted to track and target the changing shape and/or location of the tumor (for example, as the tumor moves due to normal bodily functions).

Figure 1C:
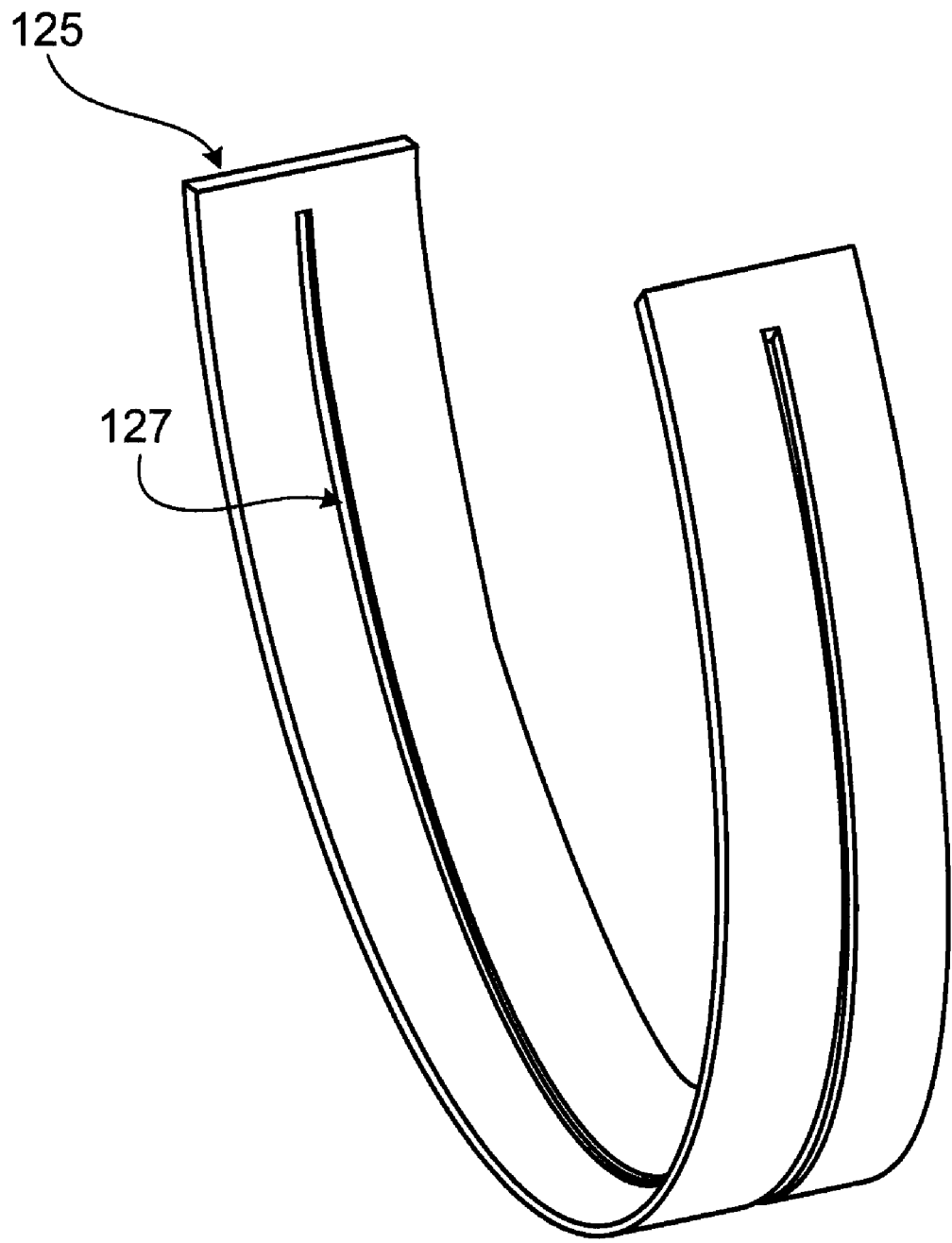
FIG. 1C illustrates an example of a collimator.

In the example shown in FIG. 1A, the electron-beam scanner 100 includes two electron guns, the electron gun 110 and the electron gun 115. Each of the electron guns 110 and 115 include a high-voltage connector that connects the electron gun 110 and the electron gun 115 to a power source. In the example shown, the electron gun 110 includes the high-voltage connector 111, and the electron gun 115 includes the high-voltage connector 116. The power source supplies a voltage sufficient to generate a voltage potential through which electrons in the electron beam are accelerated by accelerators 112 and 117 to a target (not shown), to produce x-ray radiation. The accelerators 112 and 117 may be referred to as electron accelerators. The produced x-ray radiation passes through a collimator 125, which shapes the x-ray radiation into a scan beam that can fill the region 105. Referring to FIG. 1C, the collimator 125 may be a rounded shell of a high-density material, such as lead or tungsten, that blocks x-rays. The collimator 125 includes an open slot 127 through which the x-rays generated from the electron beam striking the target pass to form an x-ray scan beam that fills the region 105. In some implementations, the scan beam may be a cone beam of x-ray radiation and the electron-beam scanner 100 may be a cone beam volumetric tomography system.

Referring again to FIGS. 1A and 1B, the object to be imaged may extend beyond the scan region 105. However, the scan region 105 may be applied to the portions of the object that are outside of the scan region 105 by moving the scan region 105 or by moving the object to be imaged into or through the scan region 105. Radiation from the scan beam that passes through the scan region 105 and through items within the scan region 105 is detected by a detection system 130 and used to generate an image of the scan region 105. The images may be three-dimensional computed tomography images.

Figure 1D:
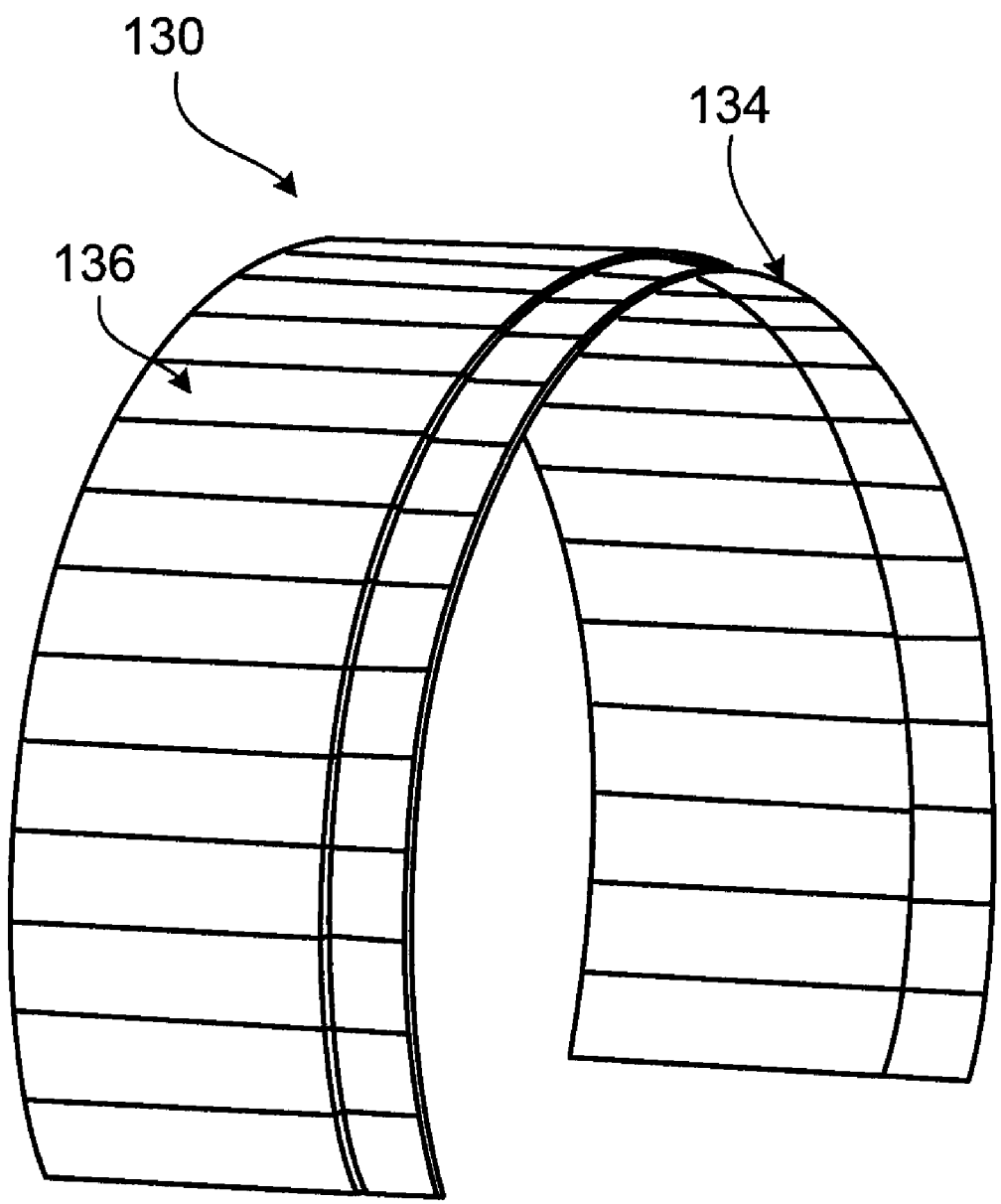
FIG. 1D illustrates an example of a detector system.

Referring to FIG. 1D, an example of the detection system 130 is shown. The detection system 130 includes a material 134 that is sensitive to the energies in the scan beam. The material 134 may be a scintillation material that is sensitive to the energies in the scan beam and converts the energies in the scan beam into light. The material 134 may be a crystalline material such as cadmium tungsten (CdW), and the material 134 may have an overall circular or semi-circular cross-section to match the circular cross section of the region 105. However, the material 134 is made up of rectangular sections, or stripes. Multiple stripes make up an arc, but the individual stripes are rectangular or otherwise linear. The detector 134 may be mounted on an arc around the region 105. For example, the material 134 may be formed as a 180-degree half-circle centered around the region 105. In other examples, the detector 134 may be formed as an arc of more than 180-degrees, such as a 210-degree arc around the region 105. The detection system 130 also includes detector board electronics 136. The detector board electronics 136 converts the radiation sensed by the material 134 into an electrical signal from which an image of the region 105 is made.

Referring again to FIGS. 1A and 1B, although the example shown in FIG. 1A includes the two electron guns 110 and 115 and the two corresponding accelerators 112 and 117, in other examples more or fewer electron guns may be used. Using more than one electron gun allows for the size of the system 100 to be reduced as compared to implementations in which one electron gun is used. For example, each electron gun may be able to scan over a distance that is determined by the distance of the electron gun from the object to be imaged and the maximum electron beam deflection angle. Thus, implementations that include one electron gun scan the x-ray beam over a relatively shorter total distance or include electron guns that are placed further from the object to be imaged in order to be able to scan the x-ray beam over a longer total distance. However, by using more than one electron gun, the electron guns may be placed closer to the object to be imaged because, together, the electron guns scan the x-ray beam over a longer distance than possible with a single electron gun scanning at the maximum deflection angle. Thus, using two electron guns results in the electron-beam scanner 100 being about half of the size of a system that uses one electron gun.

Figure 1E:
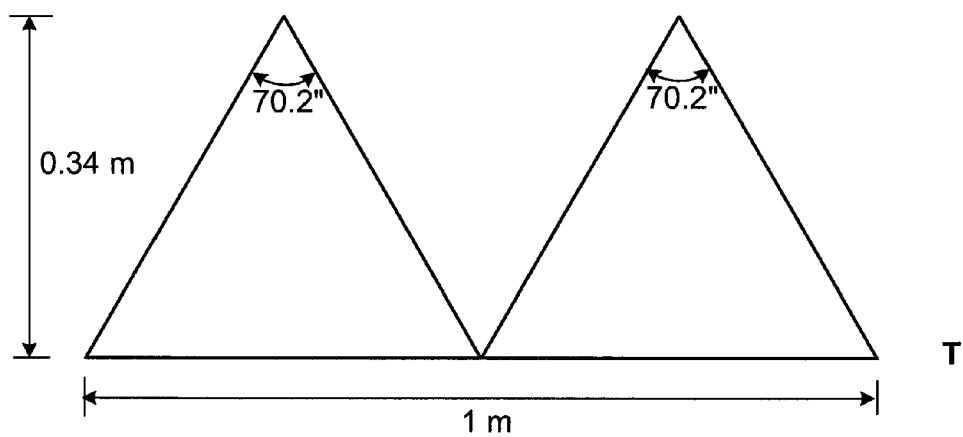
FIGS. 1E and 1F illustrate example geometries for an electron-beam scanner.
Figure 1F:
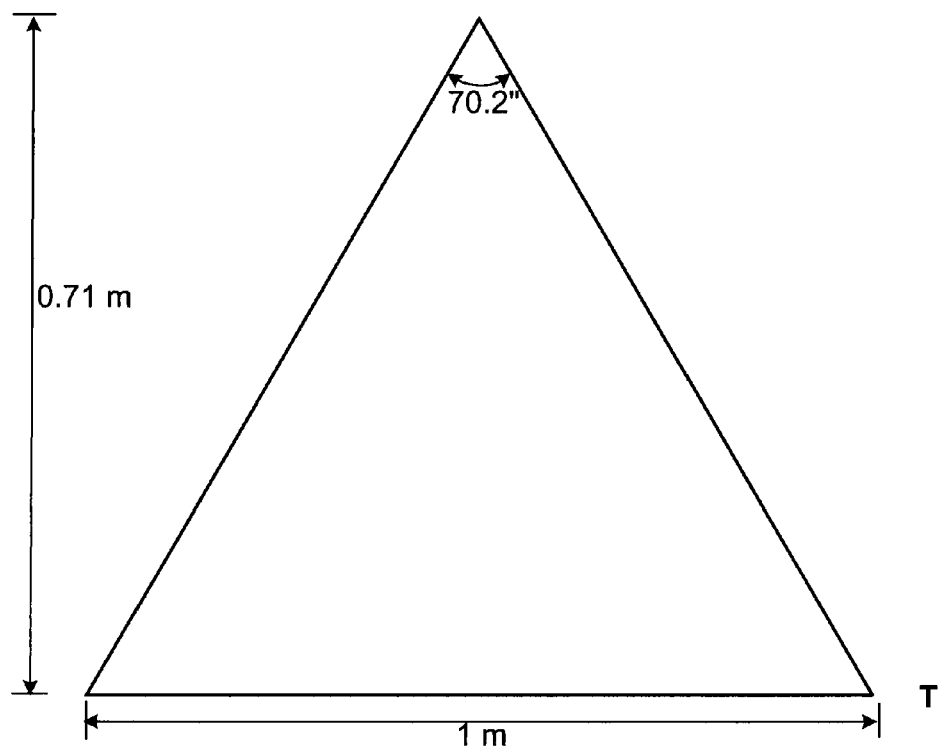

Referring to FIG. 1E, an example geometry of a system that uses two electron guns (such as the electron-beam scanner 100) is shown, and, referring to FIG. 1F, an example geometry of a system that uses one electron gun is shown. In each of the example geometries, the electron guns produce a beam having a total deflection angle of 70.2 degrees and the beam is scanned over a total distance of one meter at a target location "T." However, using the geometry shown in FIG. 1E results in a smaller system because the two electron guns are placed 0.34 meters from the target location "T" as compared to the one electron gun in the geometry shown in FIG. 1F, which is placed 0.71 meters from the target location "T." Thus, using the two electron guns 110 and 115 shown in FIG. 1A results in a smaller system to scan the same size region.

Referring to FIG. 2, an example of a linear configuration electron-beam scanner 200 is shown. The electron-beam scanner 200 scans a region 205 with a scan beam (not shown) that is generated from a first electron gun 210 and a second electron gun 215. The scan beam scans the region 205 at a rate of ten scans per second or higher (e.g., fifty scans per second) to image objects within the region 205 (such as a portion of a patient 225, a biological structure, or a tumor within the patient 225). The scan beam is a beam of radiation such as an x-ray beam. For example, the scan beam may be a cone beam of radiation and the electron-beam scanner 200 may be a cone beam volumetric tomography system.

Images generated by scanning the region 205 may be used to determine a profile of the tumor within the patient 225, even as the tumor moves, and the determined profile is used to digitally control a beam profile and position of an x-ray treatment beam used to irradiate and destroy the tumor. Objects outside of the region 205 may be imaged by the scan beam by moving the objects into the region 205 and/or by moving the region 205.

In the example shown in FIG. 2, a portion of the patient 225 is within the region 205, and the scan beam is used to image the portion of the patient 225 along with biological structures and/or other objects within the portion of the patient 225. Radiation from the scan beam that passes through the patient 225 is detected by a detection system 230 and used to generate an image of the region 205. The images may be three-dimensional computed tomography images. The detector system 230 includes a detector array that is sensitive to the energies included in the scan beam and electronics that convert the sensed energies into electrical signals that are used to generate an image of the region 205.

Because the region 205 is scanned at a rate of at least ten scans per second, structures within the patient 225 that move as a result of normal bodily functions, such a tumor in or around the patient's 225 lungs that moves continuously as the patient 225 breathes, may be imaged as the structures move. Scanning the region 205 at a rate of at least ten scans per second allows clear, non-blurred images of the moving structures to be generated.

The electron-beam scanner 200 includes two electron guns, the electron gun 210 and the electron gun 215. Each of the electron guns 210 and 215 respectively include the high-voltage connectors 211 and 216, which connect the electron gun 210 and the electron gun 215 to a power source. The power source supplies a voltage sufficient to generate a voltage potential through which electrons in the electron beam are be accelerated by accelerators 212 and 217 to a target (not shown), to produce x-ray radiation.

Although the example shown in FIG. 2 includes the two electron guns 210 and 215 and the two corresponding accelerators 212 and 217, in other examples more or fewer electron guns may be used. As discussed above with respect to FIGS. 1E and 1F, using more than one electron gun allows for the size of the system 200 to be reduced as compared to implementations in which one electron gun is used.

Figure 3:
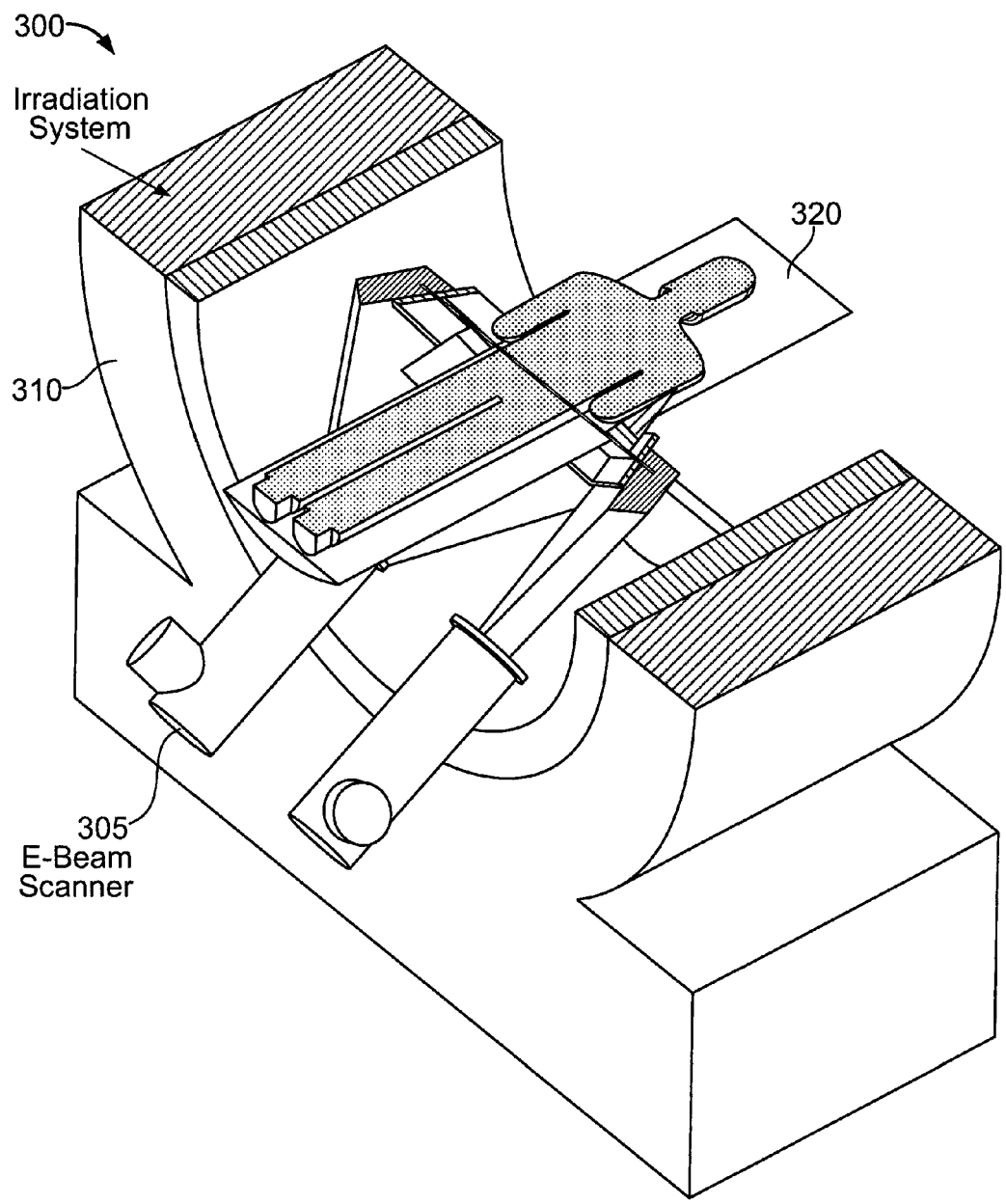
FIG. 3 illustrates a horizontal cross-section of an irradiation system that includes an electron-beam scanner.

Referring to FIG. 3, a horizontal cross-section of an irradiation system 300 that includes an electron-beam scanner 305 is shown. The irradiation system 300 also includes a gantry 310 and a patient table 320. In the example shown, the electron-beam scanner 305 is similar to the linear configuration electron-beam scanner 200 discussed with respect to FIG. 2. However, in other implementations, the electron-beam scanner 305 may be a circular configuration electron-beam scanner such as the electron-beam scanner 100 discussed with respect to FIGS. 1A and 1B. The electron-beam scanner 305 is placed in the gantry 310. The electron-beam scanner 305 is used to image a portion of the patient to, for example, image a tumor within the patient. The irradiation system 300 produces a treatment beam that is shaped and directed toward the tumor within the patient to destroy the tumor by irradiating the tumor with the treatment beam. Placing the electron-beam scanner 305 in the gantry 310 allows the treatment beam be moved with respect to the patient table 320 such that the treatment beam can be directed to the portion of the patient that includes the tumor to be destroyed. Additionally, placing the electron-beam scanner 305 in the gantry allows the scan beam to be moved and the position of the scan beam tracked with respect to the known position of the gantry 310.

Figure 4A:
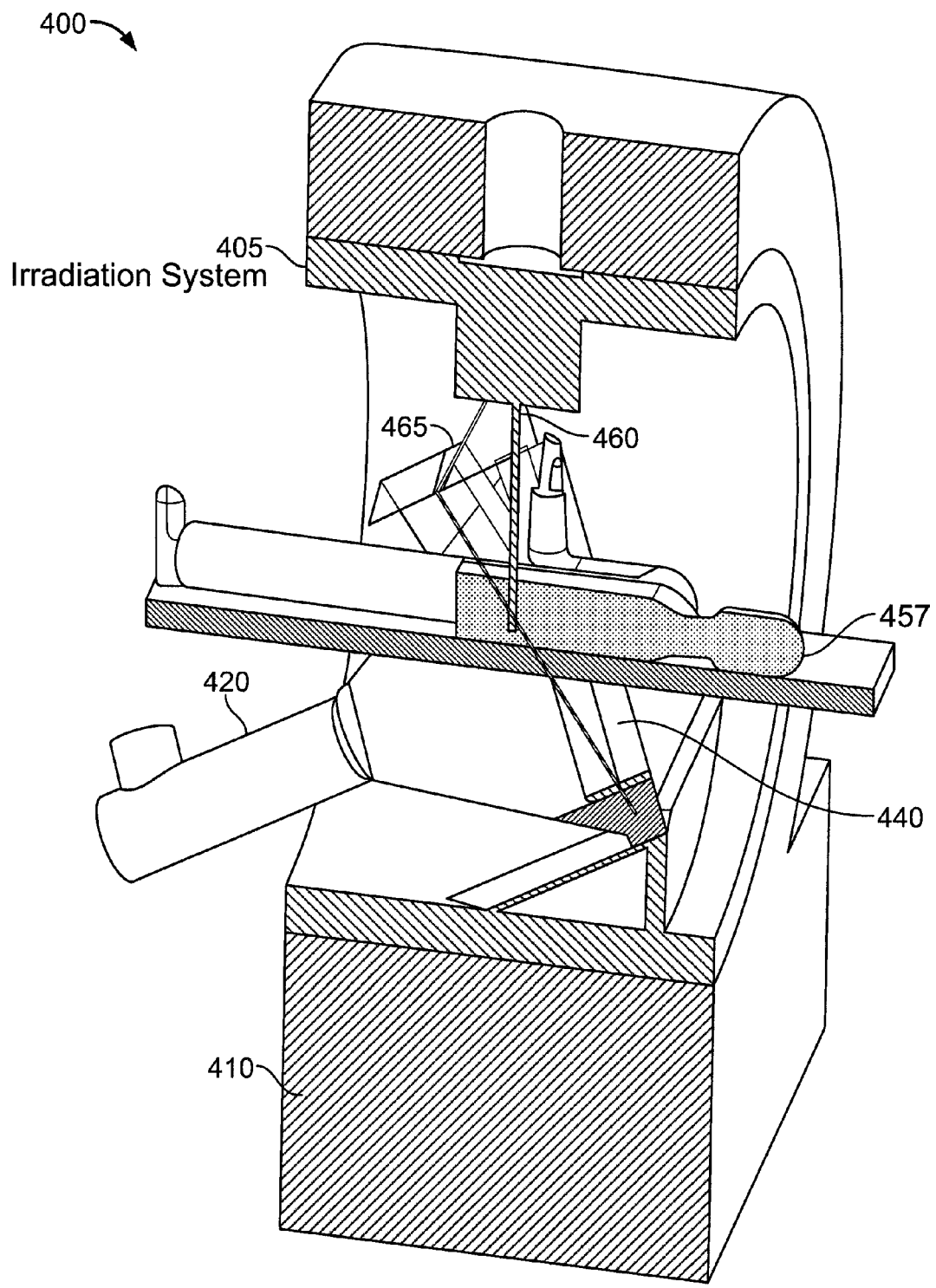
FIG. 4A illustrates a side vertical cross-section of a system that includes an irradiation system and an electron-beam scanner.
Figure 4B:
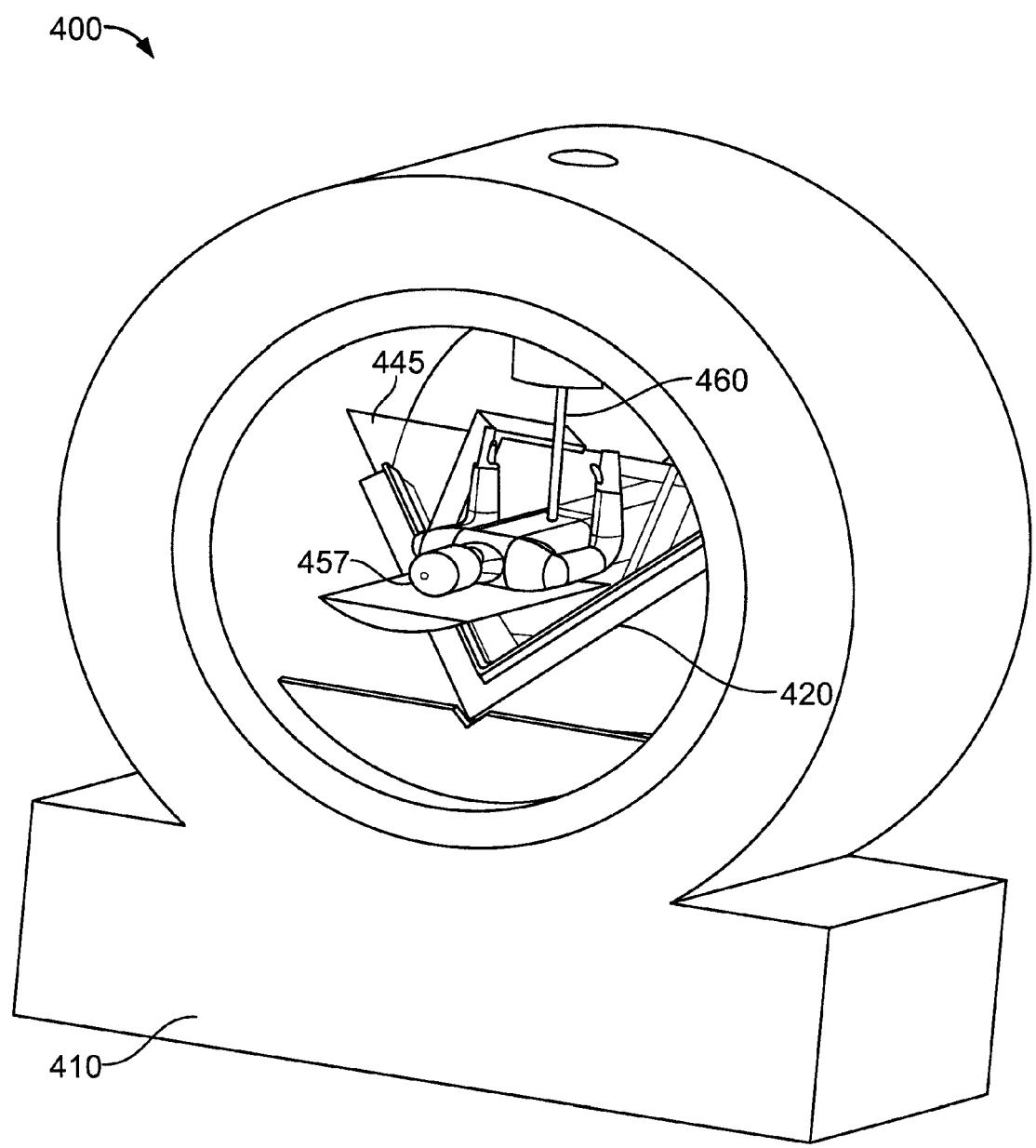
FIGS. 4B and 4D illustrate front perspective views of the system shown in FIG. 4A.

Referring to FIGS. 4A and 4B, a side vertical cross-sectional view of an example system 400 and a front perspective view of the system 400 are respectively shown. The system 400 includes an irradiation system 405 that produces a high-energy treatment beam 460 and an electron-beam scanner system that is used to image a patient 457. In the example shown in FIGS. 4A and 4B, the electron-beam scanner system is a linear configuration electron-beam scanner system similar to the electron-beam scanner system discussed above with respect to FIG. 2. The system 400 includes a gantry 410, which houses an electron-beam scan chamber 420 that produces a scan beam 440 within an x-ray beam region 445. In some implementations, the electron-beam scan chamber 420 may be removed from the gantry 410, perhaps by a robotic arm. In other implementations, the electron-beam scan chamber 420 may be permanently, or semi-permanently, affixed to the gantry 410 by, for example, bolting the electron-beam scan chamber 420 to the gantry 410.

In the example shown in FIG. 4A, images of the patient 457, and biological structures within or on the patient 457, are generated using the electron-beam scanner system. The images of the patient 457 may be volumetric computed tomography images. A high-energy x-ray beam 460, which may be referred to as a treatment beam 460, is produced by the irradiation system 405 and irradiates a target structure, such as a cancerous tumor, within the patient 457. The target structure is identified from images of the patient 457 generated by the electron-beam scanner system.

The treatment beam 460 delivers x-ray radiation to the tumor, or other target structure, while minimizing or eliminating the exposure of nearby tissue and structures to the radiation in the treatment beam 460. To minimize or eliminate the exposure of nearby tissue to the radiation in the treatment beam 460, the treatment beam 460 is shaped by a digitally controlled multi-leaf collimator and delivered to the site of the target structure as identified by the images of the tumor in the patient 457 that are generated by the electron-beam scanner system. The multi-leaf collimator may be made up of multiple segments of a material, such as lead or tungsten, that blocks energies included in the treatment beam 460. The segments of the collimator move independently, and by controlling the placement of the segments, selective portions of the treatment beam 460 may be blocked, thus controlling the shape of the beam profile of the treatment beam 460. For example, the multi-leaf collimator may include sixty-four individually controllable and moveable segments that may be moved in and out of the path of the treatment beam 460 in order to selectively block and transmit portions of the treatment beam 460. In other examples, the multi-leaf collimator may include more or fewer individually controllable and moveable segments.

Images of a target structure within the patient 457 are generated by the electron-beam scanner system and analyzed to determine the shape (or profile) of the target structure and the location of the target structure within the patient 457. In particular, images of the target structure are generated and analyzed at a rate of at least ten images per second. This allows the profile of the target structure and the location of the target structure to be tracked even if the target structure moves while the region 445 is scanned.

Additionally, the electron-beam scanner 420 may be angled at an angle 465 with respect to the treatment x-ray 460 such that detectors (such as the detectors 230) do not block the treatment beam 460 and prevent the treatment beam 460 from reaching the patient 457. The angle 465 may be defined with respect to a direction of propagation of the treatment beam 460. The scan beam 440 may be angled with respect to the treatment beam 460 by installing the electron-scanner system in the gantry 410 at the angle 465. The angle 465 may be, for example, thirty-five degrees or less, or the angle 465 may be between three and seventy-five degrees. Positioning the scan beam 440 at the angle 465 prevents the detectors from blocking the treatment beam 460. Alternatively, or additionally, the detectors may be displaced or offset laterally along the gantry 410 with respect to the treatment beam 460 such that the detectors do not block the treatment beam 460 but the detectors are still positioned close enough to the scan beam 440 to ensure that the detectors sense sufficient signal to form an image of the region 445. For example, the detectors may be displaced 100 millimeters closer to a head of the patient 457 or closer to the feet of the patient 457 with respect to the treatment beam 460.

Figure 4C:
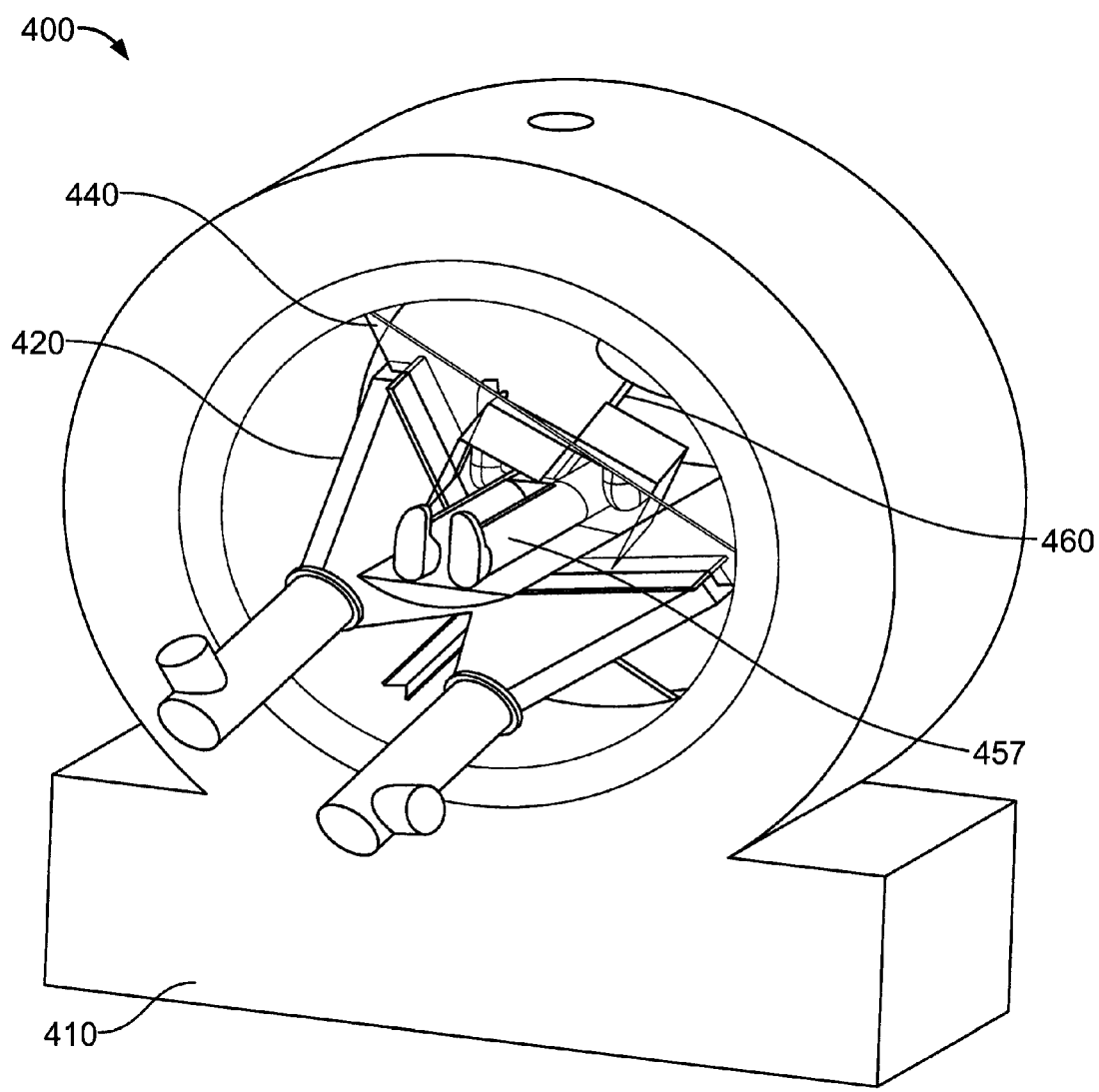
FIG. 4C illustrates a rear perspective view of the system shown in FIG. 4A.
Figure 4D:
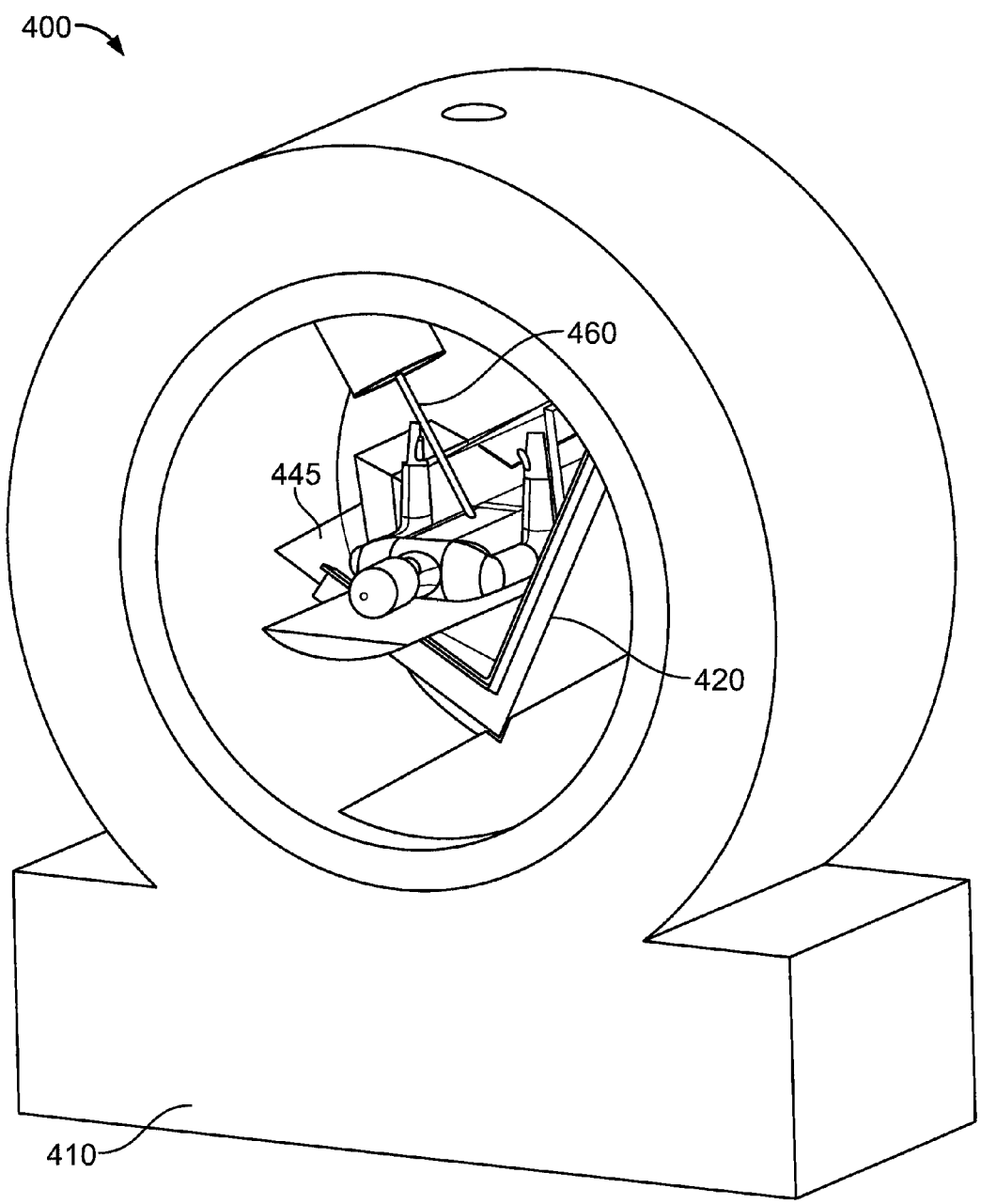

Referring to FIG. 4C, a rear perspective view of the system 400 is shown. In the example shown in FIG. 4C, the electron-beam scan chamber 420, detectors, and the treatment beam 460 are moved with respect to the patient 357 within the gantry 410 to image and irradiate different portions of the patient 457. Because the electron-beam scanner 420 and the treatment beam 460 are moved together within the gantry 410 with respect to the patient 457, the images of the region 445 remain registered with respect to the gantry 410 such that the location of the structure to be irradiated with the treatment beam 460 is known and can be targeted by the treatment beam 460. Referring to FIG. 4D, a front view of the system 400 is shown. In the example of FIG. 4D, the electron beam scan chamber 420, the x-ray beam region 445, and the treatment beam 460 have moved counter clockwise by about forty-five degrees as compared to the example shown in FIG. 4B.

Figure 5A:
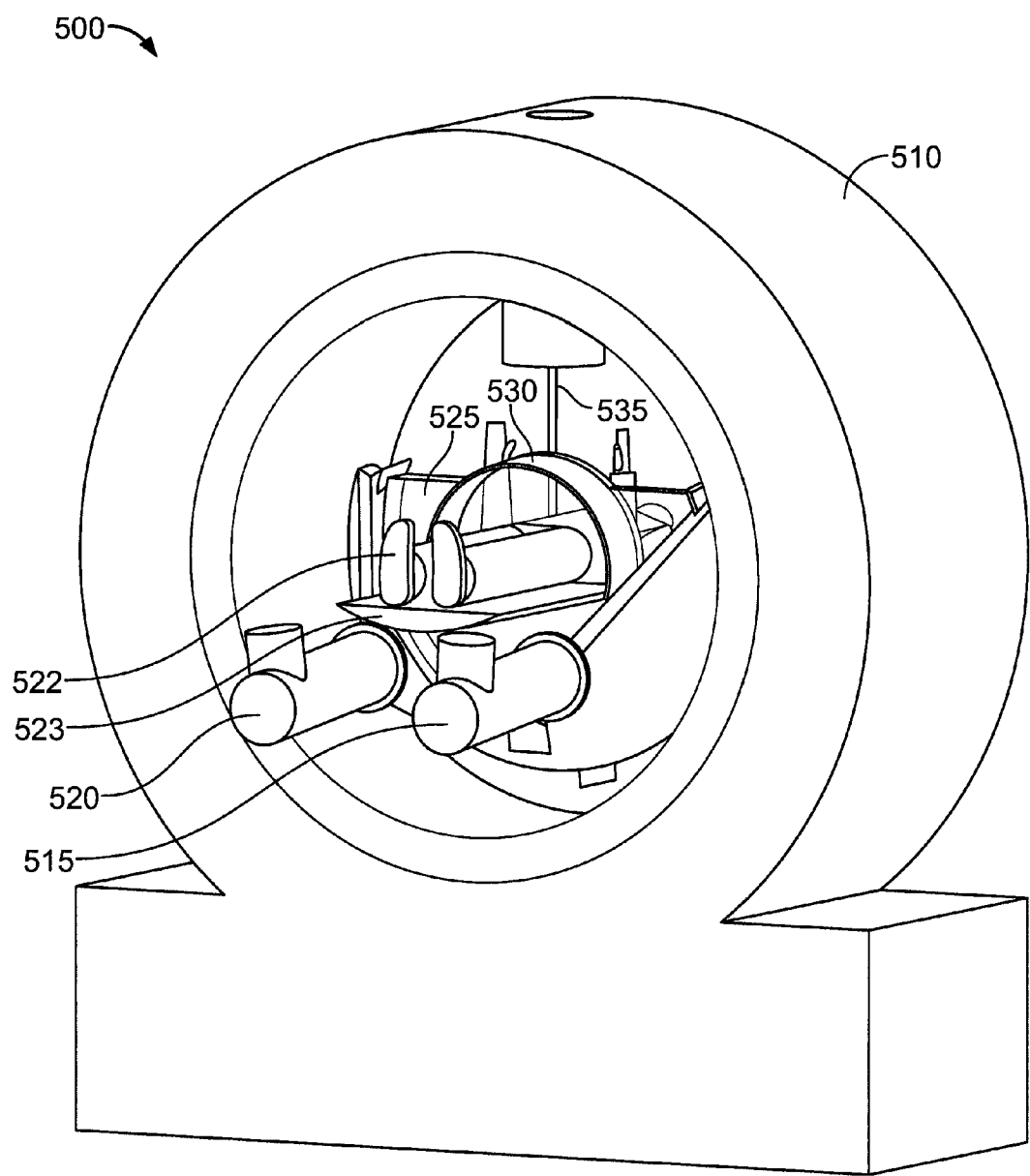
FIGS. 5A and 5B illustrate rear perspective views of another system that includes an irradiation system and an electron-beam scanner.

Referring to FIG. 5A, a vertical perspective rear view of an example system 500 that combines a circular configuration electron-beam scanner system and an irradiation system is shown. The electron-beam scanner system in the system 500 has a circular configuration that may be similar to the electron-beam scanner system 100 discussed above with respect to FIGS. 1A and 1B. The scan beam produced by the electron-beam scanner system included in the system 500 scans an object within a scan region 525. In the example shown, the electron-beam scanner system has a circular configuration and the region 525 has a circular, or semi-circular, cross-section.

The system 500 is placed within a gantry 510, and electron guns 515 and 520 generate an electron beam that is used to generate a scan beam that scans a portion of a patient 522 that is within the scan region 525 while the patient 522 rests on a table 523. Radiation from the scan beam that passes through the patient 522 is detected by a detector 530 (which may be a circular detector similar to the detector 130 discussed with respect to FIGS. 1A and 1D) to form an image of the portion of the patient 522 that is within the scan region 525 and biological structures within and/or on the patient 522. Thus, the electron-beam scanner system is used to generate images of the portion of the patient 522 that is within the region 525. Profiles of a target structure within or on the patient 522 (such as a tumor) are determined from the images, and the profiles are used to control a therapy beam 535, which is generated by the irradiation system. The therapy beam 535 may be referred to as a treatment beam 535. In particular, the profiles may be used to control the beam profile of the therapy beam 535 and direction of the therapy beam 535 such that the irradiation of the target structure is maximized while radiation to the tissue and biological structures in the vicinity of the target structure is minimized. In the example shown, the treatment beam 535 is offset from the detector 530 such that the detector 530 does not prevent the treatment beam 535 from reaching the patient 522.

Figure 5B:
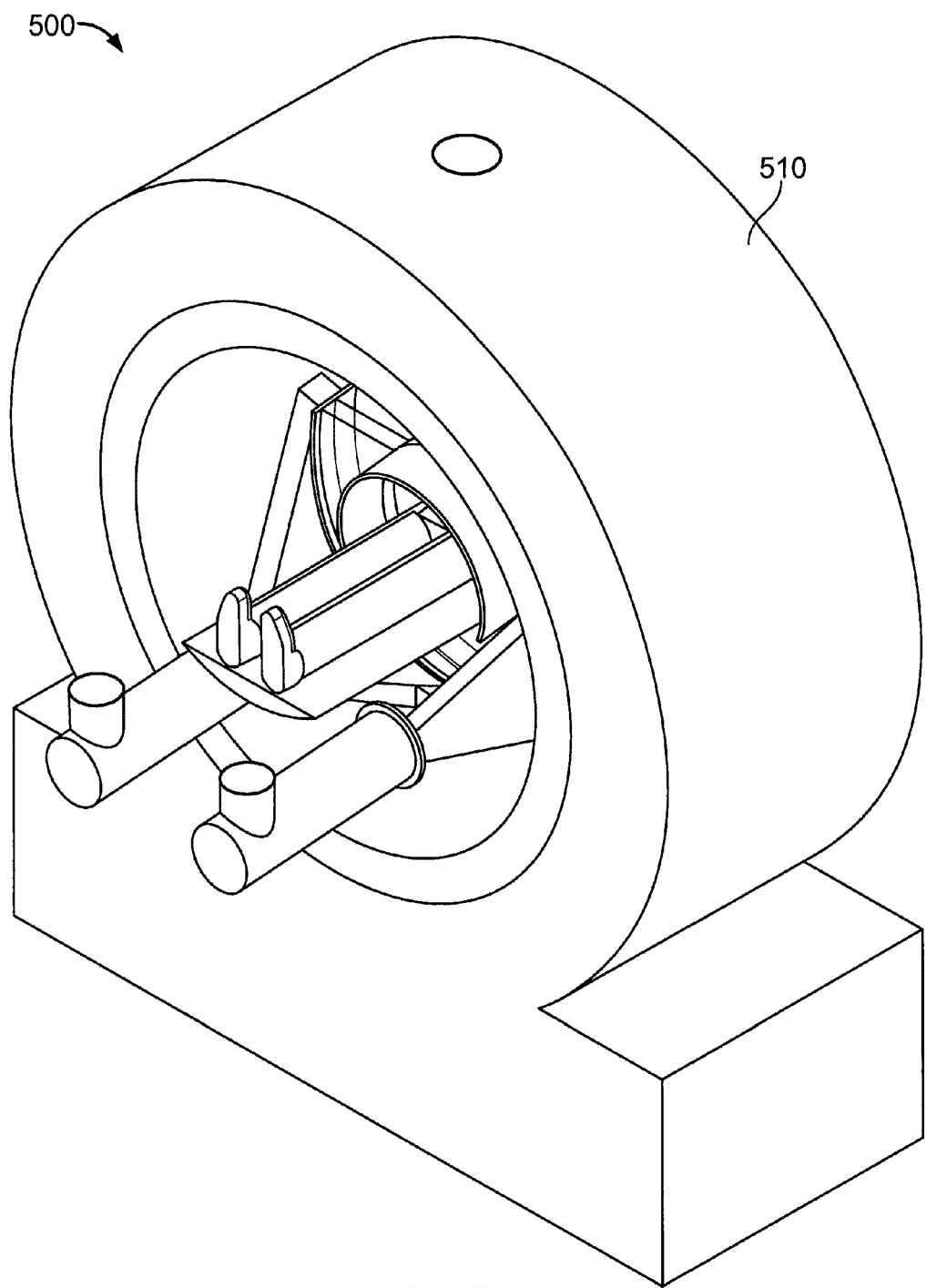
Figure 5C:
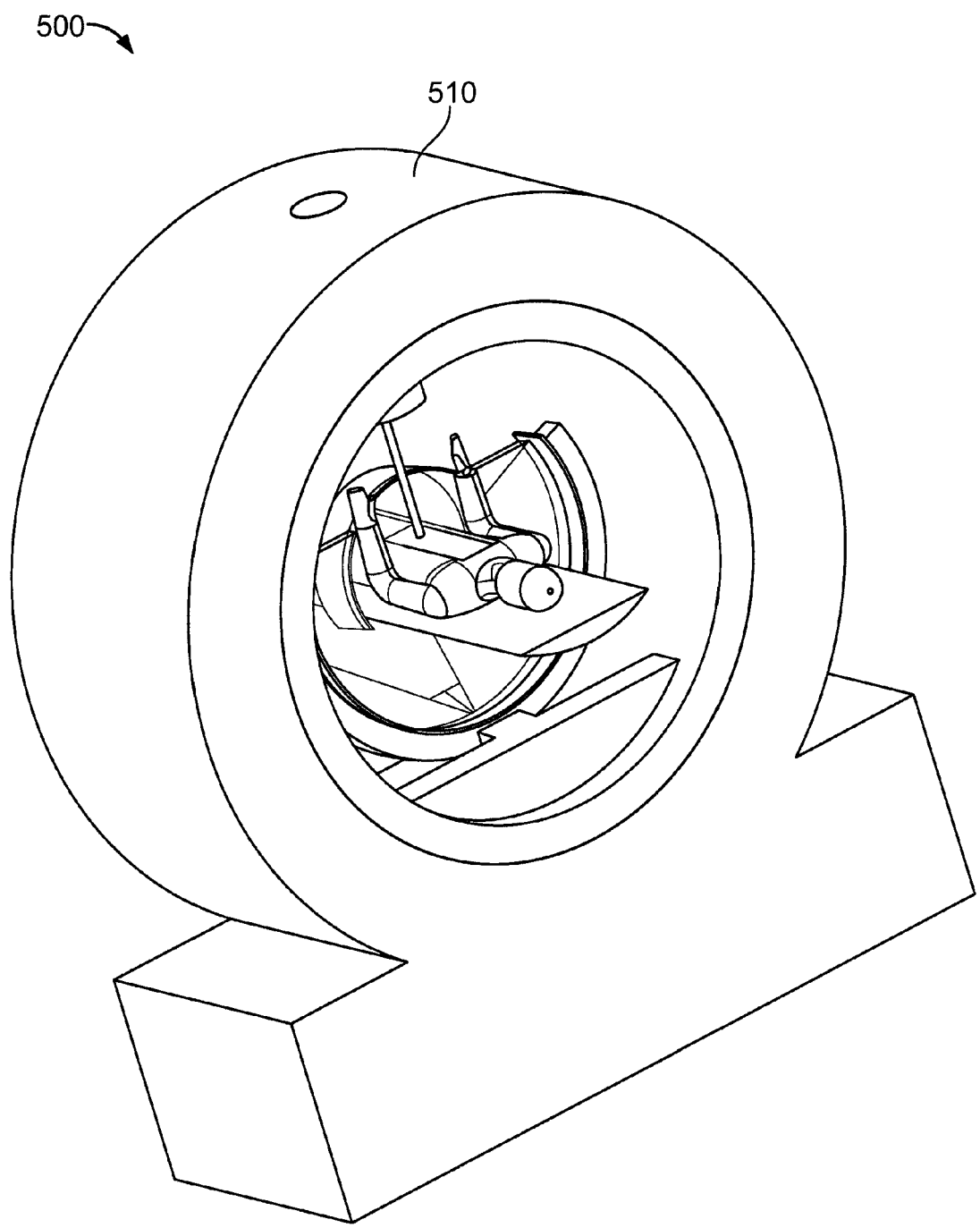
FIG. 5C illustrates a front perspective view of the system shown in FIGS. 5A and 5B.
Figure 5D:
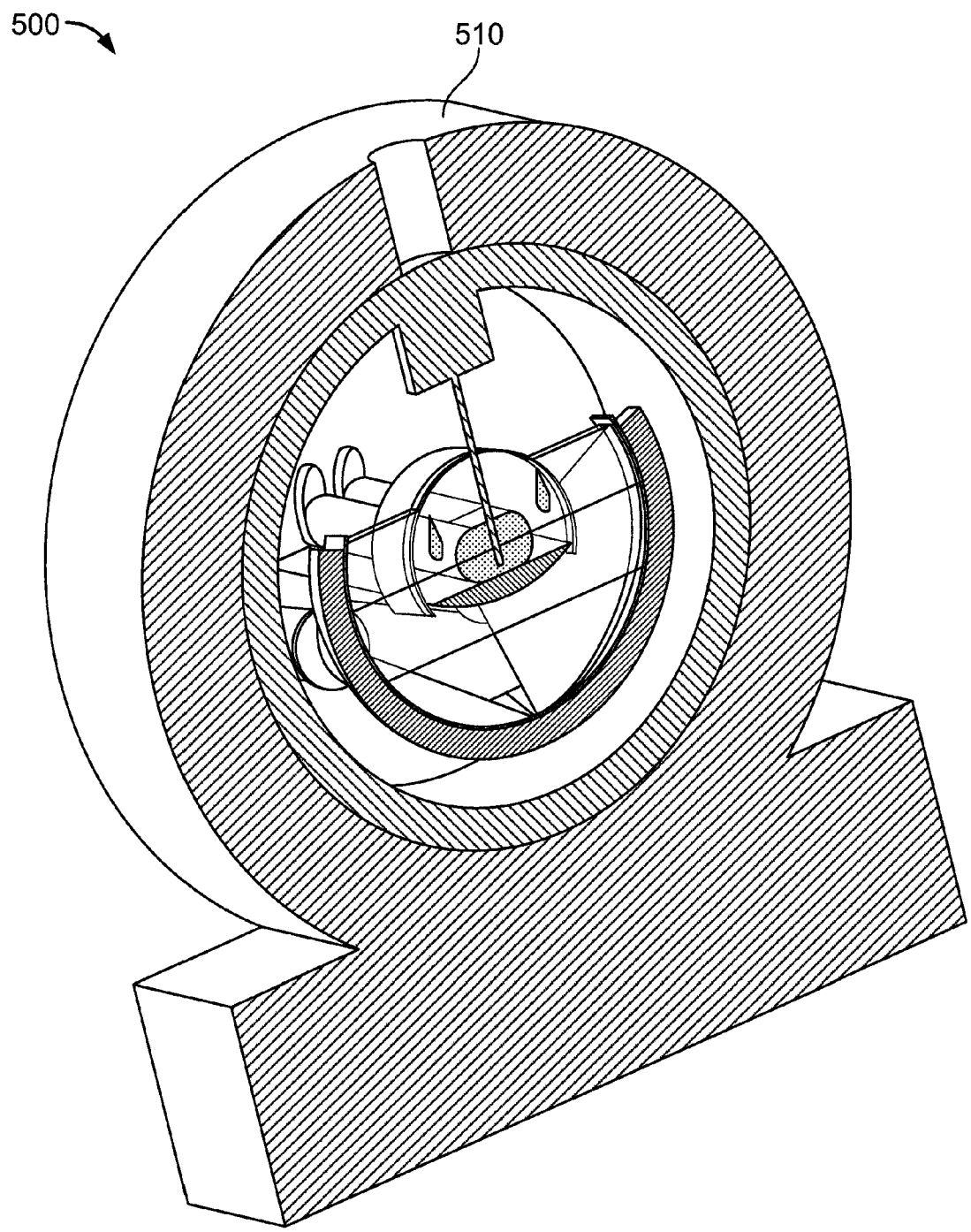
FIG. 5D illustrates a front vertical cross-sectional view of the system shown in FIGS. 5A and 5B.
Figure 5E:
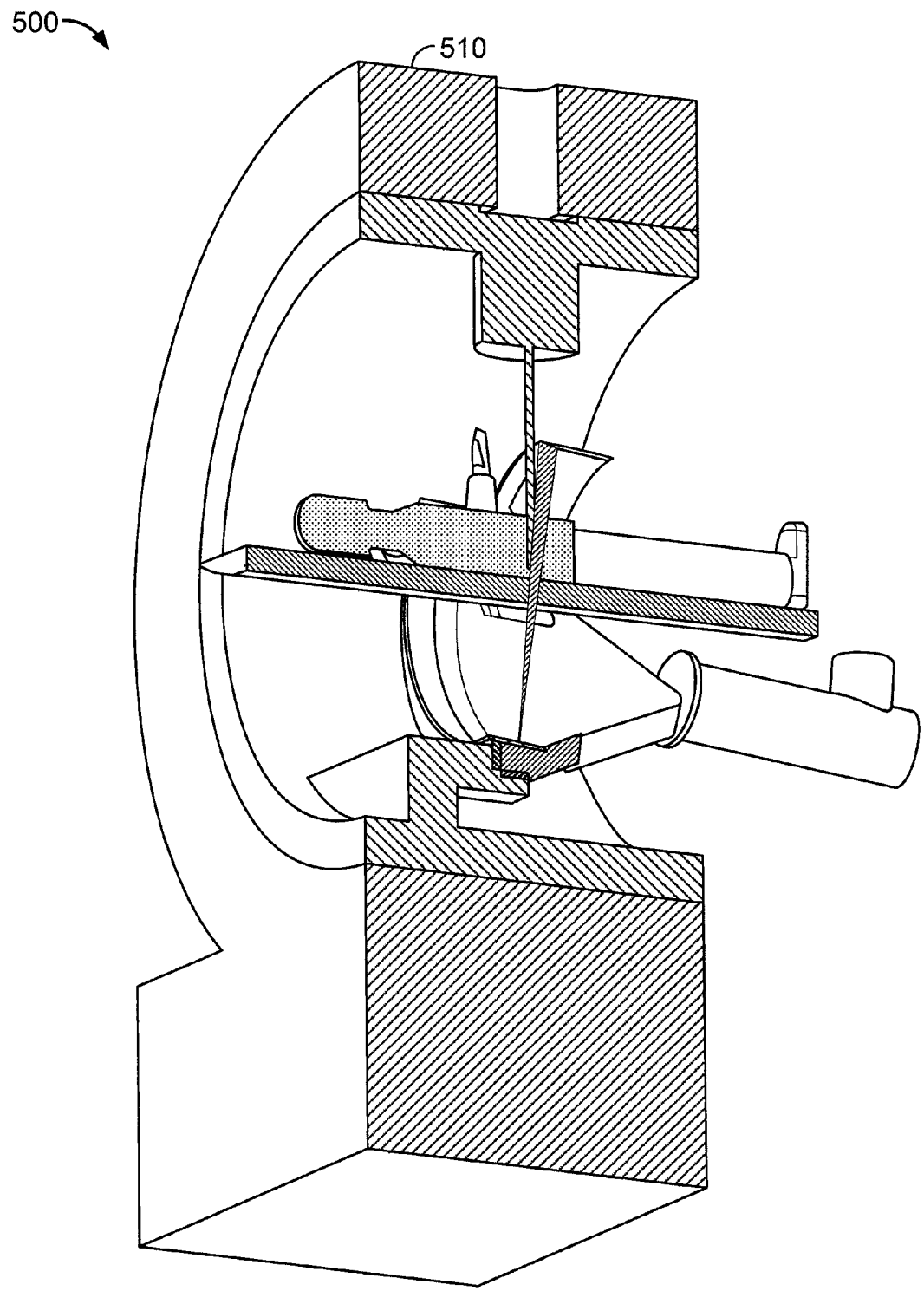
FIG. 5E illustrates a side vertical cross-sectional view of the system shown in FIGS. 5A and 5B.
Figure 5F:
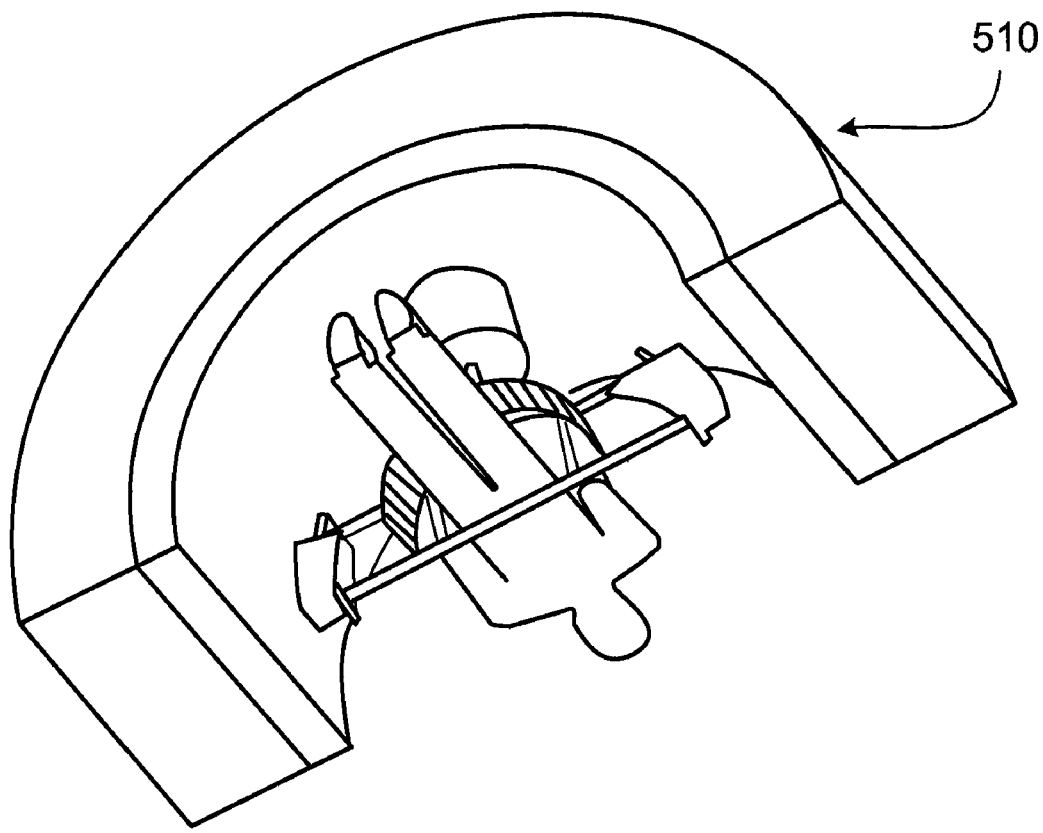
FIG. 5F illustrates a bottom cross-sectional view of the system shown in FIGS. 5A and 5B.

FIGS. 5B-5F show various views of the system 500. In particular, FIG. 5B shows a rear perspective view of the irradiation system 500, FIG. 5C shows a front perspective view of the irradiation system 500, FIG. 5D shows a front vertical cross-sectional view of the irradiation system 500, FIG. 5E shows a side vertical cross-sectional view of the irradiation system 500, and FIG. 5F shows a bottom cross-sectional view of the irradiation system 500.

Figure 6:
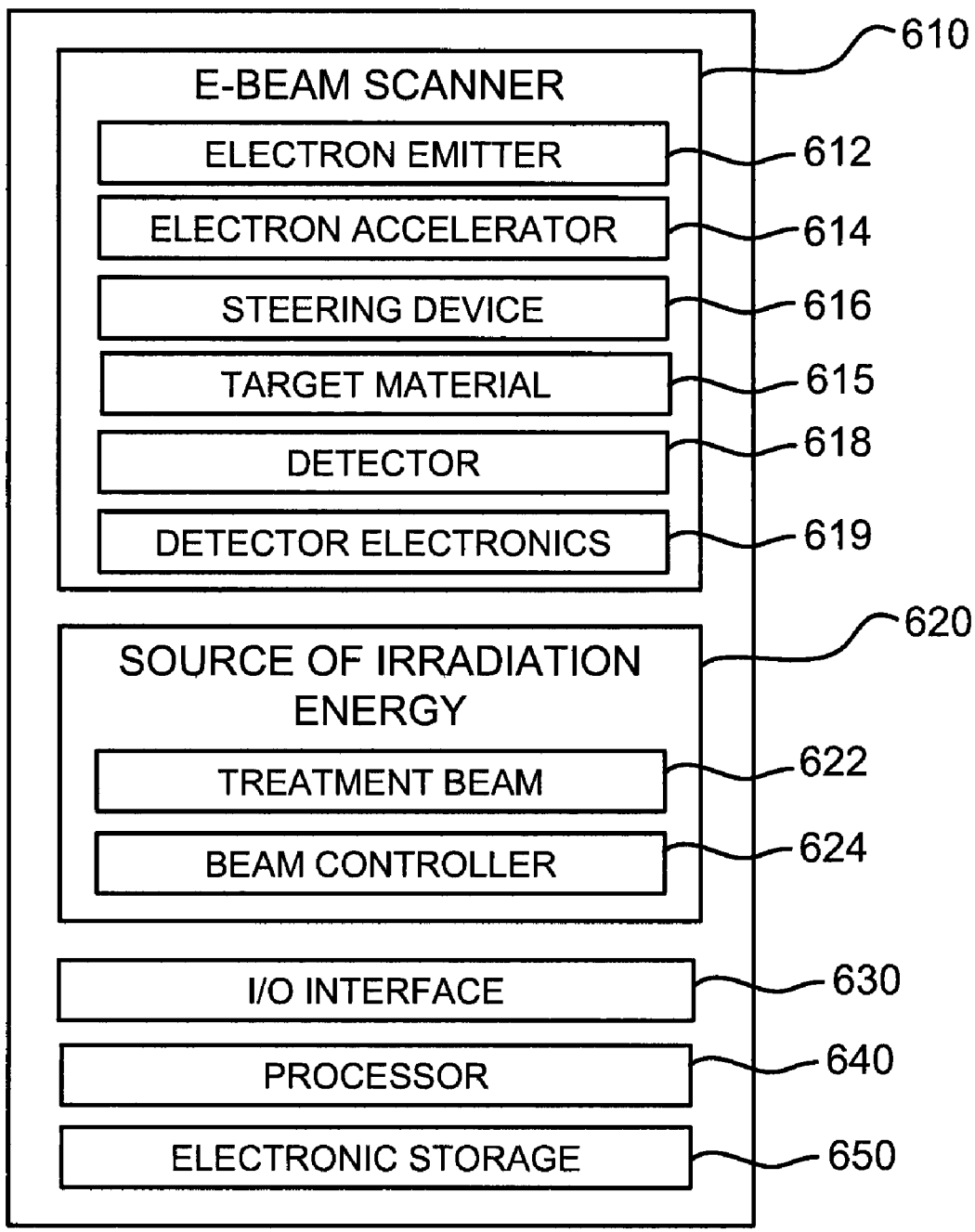
FIG. 6 is a block diagram of an example system that includes an irradiation system and an electron-beam scanner.

FIG. 6 is a block diagram of an example system that includes an irradiation system 620 and an electron-beam scanner 610. The irradiation system 600 includes an irradiation source 620 that produces a treatment beam 622. The system 600 includes an e-beam scanner 610, a source of irradiation energy 620, an input/output interface (I/O interface) 630, a processor 640, and an electronic storage 650. The e-beam scanner may be any of the e-beam scanners discussed above. In some implementations, the e-beam scanner 610 may be an e-beam scanner similar to those discussed in U.S. Pat. No. 7,428,297, which is hereby incorporated by reference in its entirety.

The e-beam scanner 610 produces an x-ray beam that is used to image a region that is also irradiated by the treatment beam produced by the source of irradiation energy 620. The e-beam scanner includes an electron emitter 612 that emits a beam of electrons, an electron accelerator 614 that accelerates the electrons in the beam of electrons, and a target material 615 that produces x-rays in response to being struck by the accelerated electrons.

The e-beam scanner 610 also includes a steering device 616, which moves the beam of electrons across the target material 615. Moving the beam of electrons across the target material 615 may also be considered scanning the beam of electrons across the target material 615 or positioning the beam of electrons at a particular place along the target material 615. Moving the beam of electrons across the target material 615 results in the x-ray beam produced by the interaction with the target material 615 having a corresponding motion relative to the portion of the region. As a result, the produced x-ray beam moves across the region to image the region or the portion of the region. The steering device 616 may include a magnet that is positionable to direct the beam of electrons in a particular direction.

Thus, in contrast to systems that use a conventional computed tomography (CT) scanner in which the source of the imaging beam itself moves, the x-ray beam produced by the e-beam scanner 610 moves through the region due to the action of the steering device 616 on the electron beam. Because the source of x-rays is not required to move (rather the x-ray beam itself is steered as a result of the electron beam being steered by the steering device 616), the e-beam scanner 610 is able to scan the region much more quickly than is possible with a conventional CT scanner system. For example, the weight of a typical CT scanner generally prevents a CT scanner from taking more than about two measurements of the imaged region per second. In contrast, the e-beam scanner 610 may take measurements fifty to one hundred times per second. Additionally, the size of the e-beam scanner 610 allows it to fit into a gantry with the source of irradiation energy to allow for concurrent imaging and treatment. Finally, the positioning of the e-beam scanner 610 and the source of irradiation energy at, for example, an angle with respect to each other or tilted with respect to each other, allows the portion of the region to be imaged with the x-ray beam produced by the e-beam scanner 610 while also being irradiated with the treatment beam 622 from the source of irradiation energy.

The e-beam scanner 610 also includes a detector 618 that senses x-ray radiation that passes through an imaged portion of a region. The imaged portion may be a portion of a human or non-human patient. For example, the imaged portion may be a suspected or known tumor within a region that includes the patient's pancreas. The detector 618 produces a representation of the sensed x-ray radiation. As compared to the x-ray radiation produced by the interaction of the electron-beam and the target material 615, the sensed x-ray radiation has an intensity that is attenuated as a result of passing through items the portion of the region. Thus, the representation of the sensed x-ray radiation represents the amount of attenuation caused by the portion of the region.

In implementations in which the detector 618 is a scintillator, the detector 618 produces visible light having an intensity proportional to the amount of detected x-ray radiation. The e-beam scanner 610 also includes detector electronics 619 that transform the representation of x-ray energy into a form that may be processed by the processor 640. For example, the detector electronics 619 may include a visible light sensor coupled to an analog-to-digital converter that produces a digital value that represents the amount of x-ray energy sensed by the detector 618.

The source of irradiation energy 620 provides a treatment beam 622 to a region that is imaged by the e-beam scanner 610. The system 600 includes both the e-beam scanner 610 and the source of irradiation energy 620, and the e-beam scanner 610 and the source of irradiation energy 620 are arranged such that the region may be imaged by the x-ray imaging beam from the e-beam scanner 610 and irradiated with the treatment beam 622 concurrently. For example, the e-beam scanner 610 may be tilted such that the treatment beam 622 and the x-ray imaging beam are at an angle with respect to each other.

The system 600 also includes the source of irradiation energy 620. The source of irradiation energy 620 produces a treatment beam 622. The source 620 also includes a beam controller 624. The beam controller 624 controls a property of the treatment beam 622. The property of the treatment beam 622 may be a profile of the treatment beam 622, an intensity of the treatment beam 622, a location of the treatment beam 622 relative to a housing of the source of irradiation energy 620, and/or a direction of propagation of the treatment beam 622. The profile of the treatment beam 622 may be a spatial distribution of energy in a plane that is perpendicular to the direction of propagation of the treatment beam 622. For example, the beam controller 624 may be a multi-leaf collimator having movable leaves that block certain portions of the treatment beam in order to shape the beam profile of the treatment beam 622. The beam controller 624 also may cause the position and/or the direction of propagation of the treatment beam 622 to change. The beam controller 624 also may control the intensity (or flux) of the treatment beam 622.

The system 600 also includes an I/O interface 630, a processor 640, and an electronic storage 650. The electronic storage 650 stores instructions, perhaps as a computer program, that, when executed, cause the processor to communicate with other components in the system 600. For example, the electronic storage 650 may store instructions that cause the beam controller 624 to move the treatment beam 622. The processor 640 executes instructions that cause the beam controller 624 to modify or otherwise adjust a property of the treatment beam based on information received from the detector 618. In another example, the electronic storage 650 stores instructions that, when executed, cause the processor 640 to generate images of the portion of the region based on the representation of sensed x-ray radiation sensed by the detector 618. The processor 640 also process commands received from the I/O interface 630. The I/O interface 630 may be any device or program that allows a user to interact with the system 600. For example, the I/O device 630 may be a mouse, a keyboard, a display, or a touch screen.

Figure 7:
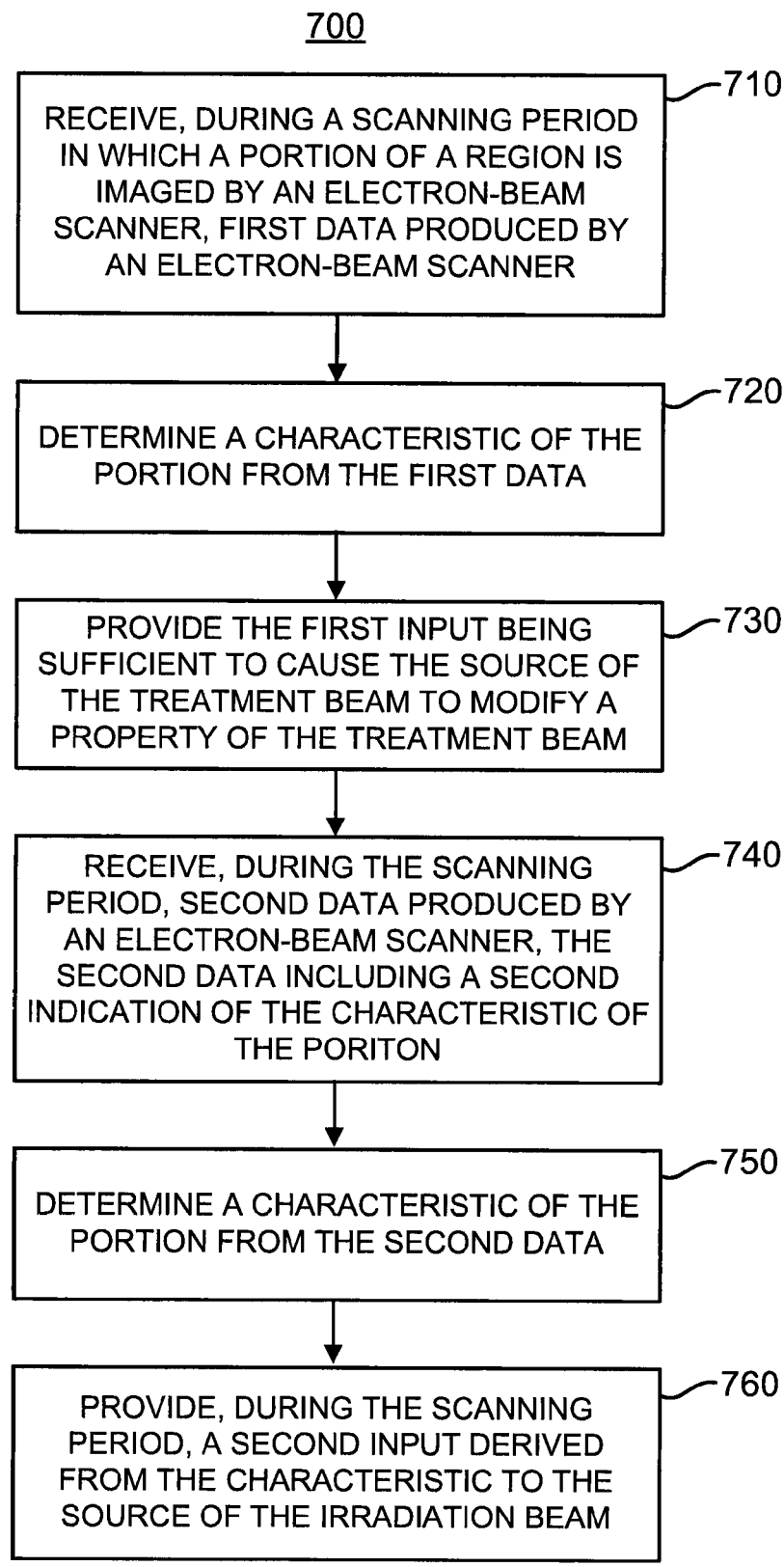
FIG. 7 is an example process for modifying a property of a treatment beam based on a characteristic of an object imaged by an electron-beam scanner.

FIG. 7 is an example process 700 for modifying a property of a treatment beam based on a characteristic of an object imaged by an electron-beam scanner. The process 700 may be performed on a processor such as the processor 640 discussed with respect to FIG. 6.

Data produced by an electron-beam scanner is received (710). The data may be referred to as "first data." The first data is received during a scanning period in which a portion of a region is imaged by the electron beam scanner 610. The first data includes an indication of a characteristic of the portion of the region. The first data may be an image, a series of images, and/or a video produced from the data sensed by the detector 618.

The region may be a portion of a patient's body, such as a pancreas, that moves continuously due to normal bodily functions, and the portion of the region may be a portion of the pancreas. As discussed above, the imaging x-ray beam produced by the electron-beam scanner 610 rapidly scans the region, which allows moving organs and other moving structures to be imaged.

The indication of the characteristic of the portion of the region may be data values that allow an analysis tool, such as an edge detector or other signal processing technique, to process the data to determine the characteristic.

The scanning period may be a time during which a patient is imaged with the x-ray imaging beam and concurrently treated with the treatment beam 622. The scanning period may be considered to be a treatment session during which a patient is treated with the treatment beam 622 to, for example, irradiate a tumor within the patient. The treatment session may be a continuous treatment session during which the patient remains in the region. The scanning period may be contrasted with techniques in which images of a portion of the region are generated and analyzed during an imaging session and then used at a later time, separate from the imaging session, to plan a treatment that uses the treatment beam 622.

A characteristic of the portion of the region is determined from the first data (620). The characteristic is determined during the scanning session. The characteristic may be a spatial characteristic, such as size, shape, an outline or partial outline, a profile, or an approximate shape that is the best match between the imaged object and a library of pre-defined shapes. For example, the characteristic may be a location, shape, and/or size of a suspected tumor within a pancreas of a patient. In another example, the shape of the tumor in a particular direction may be the characteristic. The particular direction may be a two-dimensional projection of the tumor and the organ that the tumor is within, on, or near in the direction of propagation of the treatment beam 622.

An input derived from the characteristic is provided to the irradiation source 620 (730). The input may be referred to as a "first input." The first input is sufficient to cause the irradiation source 620 to modify a property of the treatment beam 622. The property of the treatment beam 622 may be one or more of a direction of propagation of the treatment beam 622, a beam profile of the treatment beam 622, an intensity of the treatment beam 622, a timing of the treatment beam 622, and a position of the treatment beam 622. The first input may cause the source 620 to modify the treatment beam 622 by causing the beam controller 624 to move relative to the treatment beam 622. The first input is derived from the characteristic such that the input causes the treatment beam 622 to be modified to match the characteristic. For example, the characteristic may be a shape of a suspected tumor, and the treatment beam 622 may be modified to have a profile that matches the shape of the object. In another example, the treatment beam 622 may be modified by moving the treatment beam to follow, or track, the position of a moving tumor. Such modifications may increase the amount of irradiation energy that reaches the suspected tumor while decreasing the amount of radiation reaching the surrounding healthy tissue.

Data produced by the electron-beam scanner is received during the scanning period (740). This data may be referred to as second data. The second data is received after the first data, and the second data includes a second indication of the characteristic of the portion. The second data is received during the scanning period but after the first data is received. The time between receipt of the first data and the second data is determined by the scan speed of the electron-beam scanner. For example, if the electron-beam scanner receives data fifty times per second, the second data may be received approximately 20 milliseconds after the first data is received.

The characteristic of the portion is determined from the second data during the scanning period (750). For example, in implementations in which the position of the portion is the characteristic, the position is determined at the first time associated with the first data and the second time associated with the second data. Thus, the imaged portion may be tracked over time.

An input derived from the characteristic determined from the second data is provided to the source 620 (760). This input may be referred to as a second input. The second input is sufficient to cause the source 620 to modify the property of the treatment beam 622 to account for the characteristic determined from the second data, and the second input is provided during the scanning session. For example, the characteristic may be a position of a tumor in a patient's pancreas, and the second input may be an input sufficient to cause the treatment beam 622 to move to follow the tumor as it moves with the pancreas. Because of the features of the electron-beam scanner 610, the treatment beam 622 is modified during the scanning session. Thus, the treatment of the patient with the irradiation beam is planned in real-time, or near-real time, while the patient is imaged. In some implementations, the first and second input are formatted such that the inputs are compatible with inputs that are produced by a standard CT scanner.

The techniques can be implemented in digital electronic circuitry, or in computer hardware, firmware, software, or in combinations of them. The techniques can be implemented as a computer program product, i.e., a computer program tangibly embodied in an information carrier, e.g., in a machine-readable storage device, in machine-readable storage medium, in a computer-readable storage device or, in computer-readable storage medium for execution by, or to control the operation of, data processing apparatus, for example, a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

Method steps of the techniques can be performed by one or more programmable processors executing a computer program to perform functions of the techniques by operating on input data and generating output. Method steps can also be performed by, and apparatus of the techniques can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, such as, magnetic, magneto-optical disks, or optical disks. Information carriers suitable for embodying computer program instructions and data include all forms of non-volatile memory, including by way of example semiconductor memory devices, such as, EPROM, EEPROM, and flash memory devices; magnetic disks, such as, internal hard disks or removable disks; magneto-optical disks; and CD-ROM and DVD-ROM disks. The processor and the memory can be supplemented by, or incorporated in special purpose logic circuitry.

A number of implementations of the techniques have been described. Nevertheless, it will be understood that various modifications may be made. For example, useful results still could be achieved if steps of the disclosed techniques were performed in a different order and/or if components in the disclosed systems were combined in a different manner and/or replaced or supplemented by other components. Accordingly, other implementations are within the scope of the following claims.

What is claimed is:

1. A system comprising:
    an electron-beam scanner comprising:
        an electron emitter configured to produce an electron beam,
        an electron accelerator configured to accelerate the electron beam toward a target that produces an x-ray beam in response to being struck by the electron beam,
        a steering device configured to scan the electron beam along the target such that the produced x-ray beam is positioned relative to a portion of a region to be imaged, and
        a detector configured to sense x-ray radiation from the region and produce a representation of the sensed radiation;
    a source of irradiation energy configured to produce a treatment beam, wherein the electron beam scanner and the source of irradiation energy are positioned to allow the portion of the region to be exposed to the treatment beam and the produced x-ray beam concurrently; and
    a processor operable to:
        receive the representation of the sensed x-ray radiation,
        determine a characteristic of the imaged portion of the region based on the representation of the sensed x-ray radiation, and
        modify a property of the treatment beam based on the characteristic.

2. The system of claim 1, wherein the electron beam scanner is positioned at an angle relative to a direction of propagation of the treatment beam.

3. The system of claim 2, further comprising a gantry, and wherein the electron beam scanner and the source of irradiation energy are both located within the gantry.

4. The system of claim 3, wherein the electron-beam scanner is movable with respect to the gantry and the processor is further operable to determine a position of the electron-beam scanner relative to the gantry and a position of the produced x-ray beam relative to the gantry.

5. The system of claim 1, wherein the characteristic of the portion of the region comprises one or more of a position of the portion, a size of the portion, and a shape of the portion.

6. The system of claim 1, wherein the processor is further operable to generate an image of the region based on the representation of the sensed radiation.

7. The system of claim 1, wherein the portion comprises a biological structure within a human patient.

8. The system of claim 7, wherein the region comprises a pancreas, and the portion of the region comprises a portion of the pancreas.

9. The system of claim 1, wherein to control the treatment beam based on the characteristic, the processor is further operable to:

provide an input to the source of irradiation energy, the input being derived from the characteristic of the portion of the region and the input being sufficient to cause the source of irradiation energy to modify a property of the treatment beam.

10. The system of claim 9, wherein the processor provides the input to the source of irradiation energy while the produced x-ray beam illuminates the portion of the region.

11. The system of claim 9, wherein the processor provides the input to the source of irradiation energy while the portion of the region is imaged by the x-ray beam.

12. The system of claim 9, wherein the processor provides input to the source of irradiation energy during a treatment session.

13. The system of claim 9, wherein the property of the treatment beam comprises one or more of a beam profile of the treatment beam and an intensity of the treatment beam.

14. The system of claim 9, wherein the characteristic of the object comprises a size and shape of the object, and the input to the source of irradiation energy is sufficient to cause the source of irradiation energy to modify a beam profile of the treatment beam such that the profile approximately matches a size and shape of the object.

* * * * *